(12) United States Patent
Goll et al.

(10) Patent No.: US 11,202,766 B1
(45) Date of Patent: Dec. 21, 2021

(54) PHARMACEUTICAL COMPOSITIONS INCLUDING HYDROCODONE BITARTRATE AND GUAIFENESIN

(71) Applicant: ECI Pharmaceuticals, LLC, Fort Lauderdale, FL (US)

(72) Inventors: Solomon Goll, Davie, FL (US); Nirali R. Bhatt, North Lauderdale, FL (US)

(73) Assignee: ECI Pharmaceuticals, LLC, Fort Lauderdale, FL (US)

( * ) Notice: Subject to any disclaimer, the term of this patent is extended or adjusted under 35 U.S.C. 154(b) by 0 days.

(21) Appl. No.: 16/391,399

(22) Filed: Apr. 23, 2019

(51) Int. Cl.
| | |
|---|---|
| A61K 31/485 | (2006.01) |
| A61K 9/20 | (2006.01) |
| A61K 31/09 | (2006.01) |
| A61K 47/12 | (2006.01) |
| A61K 9/24 | (2006.01) |

(52) U.S. Cl.
CPC .............. *A61K 31/09* (2013.01); *A61K 9/209* (2013.01); *A61K 9/2009* (2013.01); *A61K 9/2054* (2013.01); *A61K 9/2059* (2013.01); *A61K 31/485* (2013.01); *A61K 47/12* (2013.01)

(58) Field of Classification Search
None
See application file for complete search history.

(56) References Cited

U.S. PATENT DOCUMENTS

| | | | |
|---|---|---|---|
| 10,105,324 B2 * | 10/2018 | Hafey | A61K 31/09 |
| 2003/0012820 A1 * | 1/2003 | Upadhyay | A61K 9/146 |
| | | | 424/499 |
| 2005/0266032 A1 * | 12/2005 | Srinivasan | A61K 31/137 |
| | | | 424/400 |
| 2012/0244223 A1 * | 9/2012 | Tanoue | A61K 9/0056 |
| | | | 424/490 |
| 2013/0280176 A1 * | 10/2013 | Diezi | A61K 31/485 |
| | | | 424/44 |
| 2015/0224097 A1 * | 8/2015 | Sareen | A61K 9/2031 |
| | | | 424/43 |

FOREIGN PATENT DOCUMENTS

WO    WO-2010092124 A1 *  8/2010    ......... A61K 31/7048

OTHER PUBLICATIONS

Rxlist, A webpage at rxlist.com. Retrieved on Jan. 15, 2020. Retrieved from the Internet: URL: https://www.rxlist.com/obredon-drug.htm#description>. Last reviewed Jan. 20, 2017. (Year: 2017).*

* cited by examiner

*Primary Examiner* — Robert T. Crow
*Assistant Examiner* — John P Nguyen
(74) *Attorney, Agent, or Firm* — K&L Gates LLP

(57) ABSTRACT

Novel hydrocodone bitartrate and guaifenesin pharmaceutical compositions. Methods of making and using the hydrocodone bitartrate and guaifenesin pharmaceutical compositions also are disclosed.

20 Claims, 6 Drawing Sheets

Section A-A

Section A-A

PHARMACEUTICAL COMPOSITIONS INCLUDING HYDROCODONE BITARTRATE AND GUAIFENESIN

FIELD OF THE TECHNOLOGY

The present disclosure relates to hydrocodone bitartrate and guaifenesin dosage forms and methods of making and using the same.

DESCRIPTION OF THE BACKGROUND OF THE TECHNOLOGY

The common cold is a viral infection involving the upper respiratory tract and is characterized by congestion of the mucous membranes of the nose and throat, often involving the sinuses. Uncomplicated infections usually last from three to five days. Many virus types can cause the common cold; however, the rhinoviruses are the most common type of cold virus.

Many compounds have been found effective in the relief of cold symptoms. In particular, antitussives have been found to suppress coughs. For example, hydrocodone, an opioid derived from codeine, is recognized for its antitussive effects and has been approved by the U.S. Food and Drug Administration ("FDA") to suppress coughs. Expectorants have also been found to help clear the lungs of excess mucus. For example, guaifenesin is available as an over-the-counter extended release tablet.

FDA-approved oral solutions containing hydrocodone bitartrate and guaifenesin have been available and are indicated to provide symptomatic relief of coughs and to loosen mucus associated with the common cold. Mission Pharmacal Co. markets FLOWTUSS™ oral solution containing guaifenesin and hydrocodone bitartrate. Sovereign Pharmaceuticals, LLC had marketed OBREDON™ oral solution containing guaifenesin and hydrocodone bitartrate. Other dosage forms and strengths have been sold as unapproved products. The combination of a low dose of hydrocodone and a high dose of guaifenesin is particularly effective in relieving symptoms of the common cold. Currently, there are no FDA-approved oral tablets containing hydrocodone bitartrate and guaifenesin.

Oral tablets are some of the most frequently administered dosage forms. During the manufacturing of oral tablets, it is important that each tablet contains the intended amount of drug substance, and that active is uniformly dispersed. The uniformity of the oral tablet is especially important when mixing a high-dose active ingredient with a low-dose active ingredient. Low-dose, high potency active ingredients often create issues when attempting to create a uniformly dispersed active ingredient. Particle size is an important factor in uniform dispersion of active ingredients. To ensure a uniformly dispersed, low-dose active, the active ingredient must have a particle size small enough to allow for a greater number of particles to be dispersed throughout the tablet. However, small particles can create mixing problems because they have greater surface area, resulting in stronger electrostatic forces.

In addition to particle size, size distribution can impact the bulk density of the dry mix. For example, in a mixture of small and large particles, small particles fill the gaps between the larger particles, creating a more densely packed powder. Densely packed powders often encounter flow difficulties and thus present problems during the manufacturing process. Further, particle size distribution should be consistent among different lots of the drug mixture. Variation between lots may result in potential segregation and poor homogeneity during blending and compression processes.

Accordingly, there is a need for a rapidly dissolving antitussive and expectorant combination dosage form that has acceptable content and blend uniformity.

SUMMARY

It is understood that the inventions disclosed and described in this specification are not limited to the embodiments described in this Summary.

One aspect of the present disclosure is directed to a rapidly dissolving pharmaceutical composition including: guaifenesin and hydrocodone bitartrate in a weight-to-weight ratio of about 80:1 (guaifenesin:hydrocodone); and about 1% to about 5% by weight of a disintegrant selected from crospovidone, povidone, sodium starch glycolate, croscarmellose sodium, microcrystalline cellulose, starch, pregelatinized starch, and mixtures of two or more thereof. The rapidly dissolving pharmaceutical composition also includes: about 10% to about 90% by weight of a binder selected from microcrystalline cellulose, maltodextrin, povidone, hydroxypropyl methylcellulose, hydroxyethyl cellulose, starch, pregelatinized starch, sorbitol, sucrose, and mixtures of two or more thereof; and about 0.25% to about 5% by weight of a lubricant selected from magnesium stearate, calcium stearate, zinc stearate, sodium stearate, stearic acid, lauric acid, myristic acid, palmitic acid, sodium stearyl fumaric acid, sodium stearyl fumarate, glyceryl monostearate, glyceryl tribehenate, glyceryl dibehenate, glyceryl behenate, sorbitan monostearate, sucrose monopalmitate, PEG 4000/6000, boric acid, sodium oleate, sodium benzoate, sodium acetate, sodium lauryl sulfate, magnesium lauryl sulfate, sodium chloride, talc, maize starch, corn starch, hydrous magnesium silicate, and mixtures of two or more thereof. Additionally, the rapidly dissolving pharmaceutical composition optionally includes about 0.1% to about 10% by weight of a glidant selected from talc, colloidal silicon dioxide, and mixtures of two or more thereof, and has a friability less than 1%.

Another aspect of the present disclosure is directed to a rapidly dissolving pharmaceutical composition including: guaifenesin and hydrocodone bitartrate in a weight-to-weight ratio of about 80:1 (guaifenesin:hydrocodone); and about 1% to about 5% by weight of a disintegrant selected from crospovidone, povidone, sodium starch glycolate, croscarmellose sodium, microcrystalline cellulose, starch, pregelatinized starch, and mixtures of two or more thereof. The rapidly dissolving pharmaceutical composition also includes: about 10% to about 90% by weight of a binder selected from microcrystalline cellulose, maltodextrin, povidone, hydroxypropyl methylcellulose, hydroxyethyl cellulose, starch, pregelatinized starch, sorbitol, sucrose, and mixtures of two or more thereof; about 0.25% to about 5% by weight of at least two different lubricants selected from metallic salt boundary lubricants, fatty acid boundary lubricants, fatty acid ester boundary lubricants, water insoluble boundary lubricants, and inorganic boundary lubricants; and about 0.1% to about 10% by weight of a glidant selected from the group consisting of talc, colloidal silicon dioxide, and mixtures of two or more thereof. The rapidly dissolving pharmaceutical composition may comprise a tablet having a hardness of at least 5 Kp.

Yet another aspect of the present disclosure is directed to a rapidly dissolving pharmaceutical composition including: guaifenesin and hydrocodone bitartrate in a weight-toweight ratio of about 80:1 (guaifenesin:hydrocodone); and about 1% to about 5% by weight of a disintegrant selected from crospovidone, povidone, sodium starch glycolate, croscarmellose sodium, microcrystalline cellulose, starch, pregelatinized starch, and mixtures of two or more thereof. The rapidly dissolving pharmaceutical composition also includes about 10% to about 90% by weight of a binder selected from microcrystalline cellulose, maltodextrin, povidone, hydroxypropyl methylcellulose, hydroxyethyl cellulose, starch, pregelatinized starch, sorbitol, sucrose, and mixtures of two or more thereof; about 0.25% to about 5% by weight of a lubricant selected from magnesium stearate, stearic acid, calcium stearate, sodium stearyl fumarate, hydrous magnesium silicate, talc, and mixtures of two or more thereof; and about 0.1% to about 10% by weight of a glidant selected from talc, colloidal silicon dioxide, and mixtures of two or more thereof. In addition, after a period of at least 6 months stored at a temperature ranging from 23° C. to 27° C. and a relative humidity ranging from 55% to 65%, the rapidly dissolving pharmaceutical composition retains greater than about 90% of the hydrocodone bitartrate and greater than about 90% of the guaifenesin contained in the original composition.

A further aspect of the present disclosure is directed to a rapidly dissolving pharmaceutical composition including: guaifenesin and hydrocodone bitartrate in a weight-to-weight ratio of about 80:1 (guaifenesin:hydrocodone); and about 1% to about 5% by weight of a disintegrant selected from crospovidone, povidone, sodium starch glycolate, croscarmellose sodium, microcrystalline cellulose, starch, pregelatinized starch, and mixtures of two or more thereof. The rapidly dissolving pharmaceutical composition also includes: about 10% to about 90% by weight of a binder selected from microcrystalline cellulose, maltodextrin, povidone, hydroxypropyl methylcellulose, hydroxyethyl cellulose, starch, pregelatinized starch, sorbitol, sucrose, and mixtures of two or more thereof; about 0.25% to about 5% by weight of a lubricant selected from magnesium stearate, stearic acid, calcium stearate, sodium stearyl fumarate, hydrous magnesium silicate, talc, and mixtures of two or more thereof; and about 0.1% to about 10% by weight of a glidant selected from talc, colloidal silicon dioxide, and mixtures of two or more thereof. In addition, after a period of at least 1 month stored at a temperature ranging from 38° C. to 42° C. and a relative humidity ranging from 70% to 80%, the rapidly dissolving pharmaceutical composition retains greater than about 90% of the hydrocodone bitartrate and greater than about 90% of the guaifenesin contained in the original composition.

Another aspect of the present disclosure is directed to a rapidly dissolving pharmaceutical composition comprising guaifenesin and hydrocodone bitartrate in a weight ratio of about 80:1 guaifenesin to hydrocodone bitartrate; and at least three lubricants selected from magnesium stearate, calcium stearate, zinc stearate, sodium stearate, stearic acid, lauric acid, myristic acid, palmitic acid, sodium stearyl fumaric acid, sodium stearyl fumarate, glyceryl monostearate, glyceryl tribehenate, glyceryl dibehenate, glyceryl behenate, sorbitan monostearate, sucrose monopalmitate, PEG 4000/6000, boric acid, sodium oleate, sodium benzoate, sodium acetate, sodium lauryl sulfate, magnesium lauryl sulfate, sodium chloride, talc, maize starch, corn starch, and hydrous magnesium silicate, and has a friability less than 1%. The rapidly dissolving pharmaceutical composition may comprise a tablet having a hardness of at least 5 Kp.

Another aspect of the present disclosure is directed to a method of administering a rapidly dissolving composition including guaifenesin and hydrocodone to an adult human who has ingested food within 30 minutes of administration, wherein the rapidly dissolving pharmaceutical composition provides a guaifenesin $AUC_{0\to\infty}$ ranging from about 7.42 µg*h/mL to about 8.10 µg*h/mL.

Another aspect of the present disclosure is directed to a method of preparing tablets of a rapidly dissolving pharmaceutical composition. The method comprises preparing a hydrocodone blend including adding layers of ingredients to a blender, wherein the layers include a first portion of microcrystalline cellulose, crospovidone, hydrocodone bitrate, talc, stearic acid, and a second portion of microcrystalline cellulose. The layers are blended together for 10 minutes at 15 rpm to form the hydrocodone blend. The method also comprises mixing the hydrocodone blend with Compresso GGF 95 SA by adding ingredient layers to the blender, wherein the layers include a first portion of the hydrocodone blend, Compresso GGF 95 SA, and a second portion of the hydrocodone blend. The layers are blended together for 30 minutes at 15 rpm to form a first mixture. The method further comprises adding magnesium stearate to the first mixture to form a final mixture. The final mixture is compressed into tablets.

DESCRIPTION OF THE DRAWINGS

Various features and characteristics of non-limiting and non-exhaustive embodiments disclosed and described in this specification may be better understood by reference to the accompanying figure, in which:

FIGS. 1A, 1B, and 1C are views of a high density polyethylene (HDPE) container (50 $cm^3$ to 60 $cm^3$) used to contain a pharmaceutical composition, as described herein, wherein FIG. 1A is a side exterior view including a partial sectional view of the base of the container, FIG. 1B is a sectional view of a threaded neck portion of the container shown in FIG. 1A, and FIG. 1C is an exterior view of a bottom surface of the container shown in FIGS. 1A and 1B.

FIGS. 2A, 2B, and 2C are views of a container closure that can be used in conjunction with the container shown in FIGS. 1A, 1B, and 1C, wherein FIG. 2A is an exterior side view of a ribbed, threaded closure cap, FIG. 2B is an exterior top view of the closure cap shown in FIG. 2A, and FIG. 2C is a side sectional view of the closure cap shown in FIGS. 2A and 2B.

FIGS. 4A and 4B are views of a container closure that can be used in conjunction with the container shown in FIG. 3, wherein FIG. 4A is an exterior top view of a ribbed, threaded closure cap, and FIG. 4B is a side sectional view of the cap shown in FIG. 4A.

FIGS. 6A and 6B are views of a container closure that can be used in conjunction with the container shown in FIG. 5, wherein FIG. 6A is an exterior side view of a ribbed, outer closure overcap or driver, and FIG. 6B is a side view of an inner threaded closure member that works co-operatively with the outer overcap or driver shown in FIG. 6A.

Figure 1A:
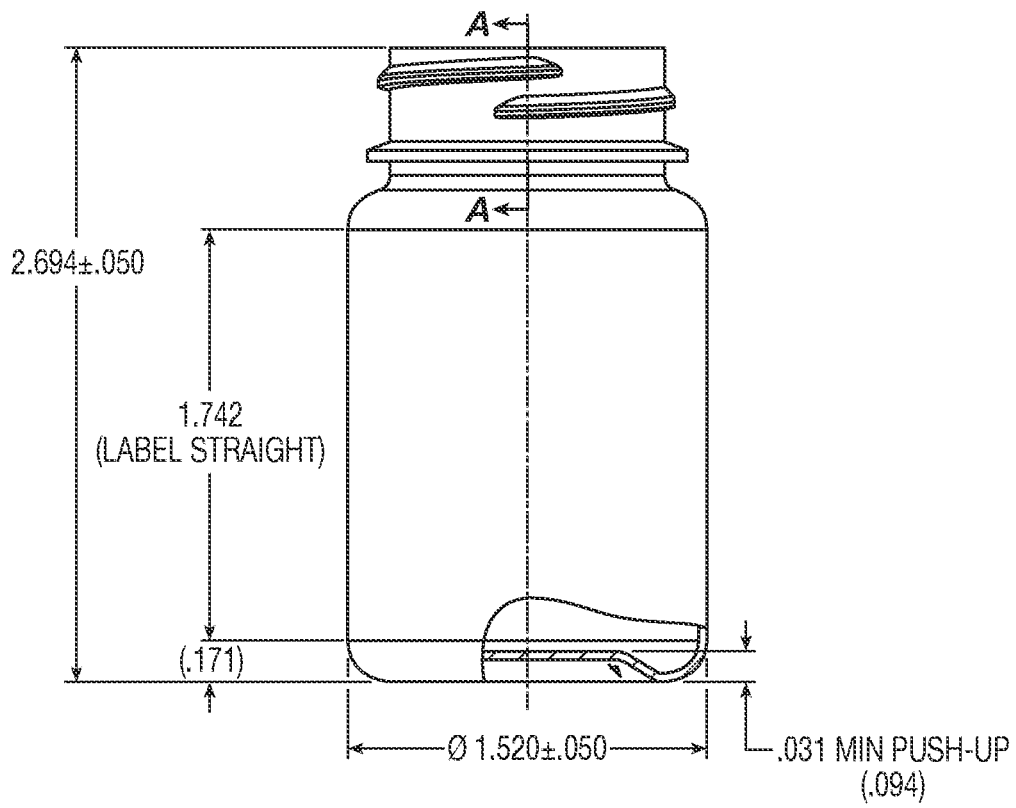

The reader will appreciate the foregoing details, as well as others, upon considering the following detailed description of various non-limiting and non-exhaustive embodiments according to the present disclosure.

DETAILED DESCRIPTION OF THE INVENTION

Generally, the present invention relates to rapidly dissolving pharmaceutical compositions comprising an expectorant and an antitussive. The expectorant can be guaifenesin. The antitussive can be hydrocodone. Hydrocodone can be present as a pharmaceutically acceptable salt. A preferred form of hydrocodone is hydrocodone bitartrate.

The compositions of the present invention can be used in the treatment of a cough, to loosen or reduce mucus, and to thin bronchial secretions.

In one aspect, a rapidly dissolving pharmaceutical composition can include an expectorant and an antitussive in a weight ratio about 80:1 expectorant to antitussive. The concentration of expectorant in the rapidly dissolving pharmaceutical composition disclosed herein is about 80% by weight. The concentration of antitussive in the rapidly dissolving pharmaceutical composition disclosed herein is about 1% by weight. In certain embodiments, a rapidly dissolving pharmaceutical composition according to the present disclosure disclosed herein includes about 400 mg of an expectorant compound and about 5 mg of an antitussive compound.

An effective dosage amount of the rapidly dissolving pharmaceutical composition of the present disclosure ranges from about 400 mg to about 1000 mg. In certain aspects, the effective dosage amount of the rapidly dissolving pharmaceutical composition can range, for example, from about 420 mg to about 950 mg, from about 400 mg to about 900 mg, from about 450 mg to about 800 mg, from about 475 mg to about 700 mg, from about 500 mg to about 650 mg, from about 400 mg to about 530 mg, from about 420 mg to about 510 mg, from about 450 mg to about 540 mg, from about 490 mg to about 530 mg, from about 480 mg to about 525 mg, or from about 490 mg to about 515 mg. The unit dosage form can be selected from tablets, capsules, granules, powder, troches, lozenges, and other suitable unit dosage forms.

The rapidly dissolving pharmaceutical composition includes at least one pharmaceutically acceptable excipient, which can be selected from, for example, one or more disintegrants, binders, lubricants, glidants, and diluents. The disintegrant can be selected from, for example, crospovidone, povidone, sodium starch glycolate, croscarmellose sodium, microcrystalline cellulose, starch, pregelatinized starch, and mixtures of two or more thereof. The binder can be selected from, for example, microcrystalline cellulose, maltodextrin, povidone, hydroxypropyl methylcellulose, hydroxyethyl cellulose, starch, pregelatinized starch, sorbitol, sucrose, and mixtures of two or more thereof.

In certain embodiments, one or more lubricants can be included in the rapidly dissolving pharmaceutical composition to aid in the tableting process. The addition of a lubricant to the rapidly dissolving pharmaceutical composition can reduce the friction between the tablet and the die metal surface, which reduces the ejection force and better ensures that the tablet is cleanly ejected without cracking or breakage. Certain factors such as, for example, lubricant type, concentration, method of lubrication, and the manner of incorporating the lubricant can affect the tablet compression process. Thus, without controlling these factors, lubricants may cause undesirable changes in the properties of tablets.

Several types of boundary lubricants can be used as excipients in the rapidly dissolving pharmaceutical compositions including, for example, metallic salts of fatty acids, fatty acids, hydrocarbons, fatty alcohols, fatty acid esters, alkyl sulfates, polymers, and inorganic materials. A lubricant included in the present compositions can be selected from, for example, magnesium stearate, stearic acid, calcium stearate, sodium stearyl fumarate, hydrous magnesium silicate, talc, and mixtures of two or more thereof.

The inventors discovered differences in the interactions between lubricants and the particles of the present rapidly dissolving pharmaceutical compositions that can affect flowability. Lubricants included in the present compositions can be mixed with other excipients in varying amounts to control and affect flowability. In certain embodiments, the lubricant can be a combination of boundary lubricants to enhance the powder flow and tableting properties of the rapidly dissolving pharmaceutical composition. In certain embodiments, the lubricant can include at least one lubricant, at least two different lubricants, at least three different lubricants, or a mixture of at least three lubricants. For example, the lubricant can include at least one of magnesium stearate, stearic acid, and hydrous magnesium silicate or talc.

In certain embodiments, the glidant included in a rapidly dissolving pharmaceutical composition according to the present disclosure can be selected from hydrous magnesium silicate or talc, colloidal silicon dioxide, and mixtures thereof. In certain embodiments, a diluent included in a rapidly dissolving pharmaceutical composition according to the present disclosure can be selected from, for example, povidone, starch, pregelatinized starch, microcrystalline cellulose, lactose, sorbitol, mannitol, sucrose, talc, and mixtures of two or more thereof. Other examples of suitable excipients that may be included in certain embodiments of the compositions herein are listed in Kibbe, Arthur H., "Handbook of Pharmaceutical Excipients" (3rd ed.) (2000), and Gennaro, A. R., "Remington: The Science and Practice of Pharmacy" (edited by Lippincott, Williams, & Wilkins, 20th ed.) (2000), both which are incorporated by reference herein.

The amount of one or more disintegrants contained in the rapidly dissolving pharmaceutical compositions according to the present disclosure can range from 5 mg to about 25 mg. In certain aspects, the amount of the one or more disintegrants contained in the rapidly dissolving pharmaceutical composition can range from about 2.0 mg to about 30 mg, from about 3.0 mg to about 28 mg, from about 4.0 mg to about 10 mg, or from about 5.0 mg to about 15 mg. The concentration of one or more disintegrants contained in the rapidly dissolving pharmaceutical compositions according to the present disclosure can range from about 1.0% to about 5.0%, by weight based on the total weight of the rapidly dissolving pharmaceutical composition. In certain aspects, the concentration of one or more disintegrants contained in the rapidly dissolving pharmaceutical compositions according to the present disclosure can range from about 0.10% to about 7.0%, from about 0.30% to about 6.0%, from about 0.40% to about 4.0%, from about 0.50% to about 3.5%, or from about 0.70% to about 2.0%, all in weight percentages based on the total weight of the rapidly dissolving pharmaceutical composition.

The amount of one or more binders contained in the rapidly dissolving pharmaceutical compositions according to the present disclosure can range from about 50 mg to about 455 mg. In certain embodiments, the amount of one or more binders contained in the rapidly dissolving pharmaceutical compositions according to the present disclosure can range from about 15 mg to about 500 mg, from about 25 mg to about 300 mg, from about 30 mg to about 200 mg, from about 40 mg to about 100 mg, from about 45 mg to about 80 mg, from about 20 mg to about 80 mg, from about 35 mg to about 75 mg, from about 40 mg to about 60 mg, or from about 45 mg to about 200 mg. In certain embodiments, the concentration of one or more binders contained in the rapidly dissolving pharmaceutical compositions according to the present disclosure can range from about 10% to about 90%, by weight based on the total weight of the rapidly dissolving pharmaceutical composition. In certain embodiments, the amount of one or more binders contained in the rapidly dissolving pharmaceutical compositions according to the present disclosure can range from about 5.0% to about 95%, from about 7.0% to about 80%, from about 8.0% to about 75%, from about 10% to about 70%, or from about 20% to about 60%, by weight based on the total weight of the rapidly dissolving pharmaceutical composition.

The amount of one or more lubricants contained in the rapidly dissolving pharmaceutical compositions according to the present disclosure can range from about 1.25 mg to about 25 mg. In certain embodiments, the amount of one or more lubricants contained in the rapidly dissolving pharmaceutical compositions can range from about 2.0 mg to about 20 mg, from about 2.5 mg to about 15 mg, from about 3.0 mg to about 12 mg, or from about 5 mg to about 10 mg. In certain embodiments, the concentration of one or more lubricants contained in the rapidly dissolving pharmaceutical compositions herein can range from about 0.25% to about 5.0%, by weight based on the total weight of the rapidly dissolving pharmaceutical composition. In certain embodiments, the concentration of one or more lubricants contained in the rapidly dissolving pharmaceutical compositions herein can range from about 0.20% to about 6.0%, from about 0.40% to about 4.0%, from about 0.50% to about 3.0%, or from about 0.75% to about 2.0%, by weight based on the total weight of the rapidly dissolving pharmaceutical composition.

In certain embodiments, metallic salt boundary lubricants can be used independently or in combination with other types of lubricants to improve tableting of the rapidly dissolving pharmaceutical compositions. For example, the metallic salt boundary lubricant magnesium stearate is relatively inexpensive, provides high lubrication, has a high melting point, and is chemically stable. In certain embodiments, a metallic salt boundary lubricant included in a rapidly dissolving pharmaceutical composition according to the present disclosure can be selected from, for example, magnesium stearate, sodium stearyl fumarate, calcium stearate, and zinc stearate. Since sodium stearyl fumarate is often supplied in a purer form, it can provide an option when the less pure stearate-type lubricants (stearic acid and magnesium stearate) cannot be used due to chemical incompatibility. Metallic salt lubricants can be added to the rapidly dissolving pharmaceutical compositions herein in a range from about 0.05% to about 2.5%, from about 0.1% to about 1.5%, from about 0.15% to about 1.75%, or from about 0.25% to about 1.0%, by weight based on the total weight of the rapidly dissolving pharmaceutical composition.

The present inventors observed that because many lubricants are hydrophobic, tablet disintegration and dissolution rates may be reduced by the addition of a lubricant. In some embodiments, magnesium stearate can have increased negative effects on the hardness of the tablets when combined with deformable materials (e.g., microcrystalline cellulose) compared with combinations with brittle materials. For example, when magnesium stearate is mixed with microcrystalline cellulose, tablet strength can be weakened significantly as the amount of added lubricant is increased. Thus, the preferred concentration range of magnesium stearate added as a lubricant to the rapidly dissolving pharmaceutical compositions herein is from about 0.25% to about 1.0%, by weight based on the total weight of the rapidly dissolving pharmaceutical composition.

Fatty acid boundary lubricants can be also used as a lubricant for tableting of the rapidly dissolving pharmaceutical compositions herein. For example, it has been observed that the fatty acid boundary lubricant stearic acid is a more effective die lubricant than the corresponding alcohols, and the alcohols are better than the corresponding hydrocarbons. In certain embodiments, a fatty acid boundary lubricant included in a rapidly dissolving pharmaceutical composition according to the present disclosure can be selected from, for example, stearic acid, lauric acid, myristic acid, palmitic acid, and sodium stearyl fumaric acid. Fatty acid ester boundary lubricants also can be used in the preparation of the dosage forms herein. In certain embodiments, a fatty acid ester boundary lubricant included in a rapidly dissolving pharmaceutical composition according to the present disclosure can be selected from, for example, sodium stearyl fumarate, glyceride esters such as glyceryl monostearate, glyceryl tribehenate, and glyceryl dibehenate, as well as sugar esters such as sorbitan monostearate and sucrose monopalmitate. Fatty acid and/or fatty acid ester boundary lubricants can be added to the rapidly dissolving pharmaceutical compositions according to the present disclosure in a range of, by weight, from about 0.05% to about 4.0%, from about 0.1% to about 3.7%, from about 0.15% to about 3.5%, from about 0.5% to 3.1%, from about 1.0% to about 3.0%, from about 1.5% to about 2.5%, or preferably about 2.5%, by weight based on the total weight of the rapidly dissolving pharmaceutical composition.

In certain embodiments, water soluble boundary lubricants can be used independently or in combination with other types of lubricants to improve tableting of the rapidly dissolving pharmaceutical compositions. In certain embodiments, a water soluble boundary lubricant included in a rapidly dissolving pharmaceutical composition according to the present disclosure can be selected from, for example, CARBOWAX® PEG 4000/6000, boric acid, sodium oleate, sodium benzoate, sodium acetate, sodium lauryl sulfate, magnesium lauryl sulfate, and sodium chloride. Water soluble boundary lubricants can be added to the rapidly dissolving pharmaceutical compositions according to the present disclosure in a range of, by weight, from about 0.7% to about 11%, from about 1.0% to about 10%, from about 2.0% to about 9.0%, from about 3.0% to about 8.0%, from about 4.0% to about 7.0%, from about 5.0% to about 8.0%, from about 1.5% to about 8%, from about 2.0% to about 7.0%, from about 2.5% to about 10%, from about 4.0% to about 10%, from about 5.0% to about 11%, or from about 3.0% to about 9.0%, by weight based on the total weight of the rapidly dissolving pharmaceutical composition.

In certain embodiments, water insoluble boundary lubricants can be used independently or in combination with other types of lubricants to improve tableting of the rapidly dissolving pharmaceutical compositions. In certain embodiments, a water insoluble boundary lubricant included in a rapidly dissolving pharmaceutical composition according to the present disclosure can be selected from, for example, a metal stearate (e.g., magnesium stearate, calcium stearate, and sodium stearate), stearic acid, talc, glyceryl behenate, maize starch, corn starch, STEAR-O-WET®, and STEROTEX®. Water insoluble boundary lubricants can be added to the rapidly dissolving pharmaceutical compositions according to the present disclosure in a range of, by weight, from about 0.7% to about 11%, from about 1.0% to about 10%, from about 2.0% to about 9.0%, from about 3.0% to about 8.0%, from about 4.0% to about 7.0%, from about 5.0% to about 8.0%, from about 1.5% to about 8%, from about 2.0% to about 7.0%, from about 2.5% to about 10%, from about 4.0% to about 10%, from about 5.0% to about 11%, or from about 3.0% to about 9.0%, by weight based on the total weight of the rapidly dissolving pharmaceutical composition.

Suitable lubricant excipients for addition to the rapidly dissolving pharmaceutical composition can also include, for example, an inorganic boundary lubricant. For example, an inorganic boundary lubricant such as hydrous magnesium silicate, boric acid, or talc is useful as a lubricant when other lubricants cannot be used due to chemical instabilities. Inorganic boundary lubricants can be added to the rapidly dissolving pharmaceutical composition herein for use as a tablet lubricant in a range of from about 0.05% to about 15%, from about 0.1% to about 14%, from about 0.15% to about 13%, from about 0.5% to 12%, from about 1% to about 11%, or preferably from about 1.0% to about 10%, by weight based on the total weight of the rapidly dissolving pharmaceutical composition.

The amount of one or more glidants contained in certain embodiments of the rapidly dissolving pharmaceutical compositions herein can range from about 0.5 mg to about 50 mg. In certain embodiments, the amount of one or more glidants contained in the rapidly dissolving pharmaceutical composition according to the present disclosure can range from about 0.25 mg to about 75 mg, from about 0.4 mg to about 60 mg, from about 0.6 mg to about 40 mg, from about 0.75 mg to about 30 mg, from about 1.0 mg to about 20 mg, from about 1.5 to about 10 mg, from about 2.0 mg to about 8 mg, or from about 4.0 mg to about 15 mg. In certain embodiments, the concentration of one or more glidants contained in the rapidly dissolving pharmaceutical compositions herein can range from about 0.1% to about 10%, by weight based on the total weight of the rapidly dissolving pharmaceutical composition. In certain embodiments, the concentration of one or more glidants contained in the rapidly dissolving pharmaceutical composition herein can range from about 0.10% to about 15%, from about 0.3% to about 12%, from about 0.5% to about 11%, from about 1.0% to about 10%, from about 0.25% to about 8%, from about 0.3% to about 5%, from about 0.4% to about 4%, from about 0.75% to about 3%, or from about 1% to about 3%, by weight based on the total weight of the rapidly dissolving pharmaceutical composition. In certain embodiments, the glidant can include hydrous magnesium silicate or talc in a concentration range preferably from about 1.0% to about 10%, by weight based on the total weight of the rapidly dissolving pharmaceutical composition.

The amount of one or more diluents contained in the rapidly dissolving pharmaceutical compositions according to the present disclosure can range from 2.5 mg to about 126 mg. In certain embodiments, the amount of one or more diluents contained in the rapidly dissolving pharmaceutical compositions herein can range from about 3.0 mg to about 120 mg, from about 5 mg to about 100 mg, from about 15 mg to about 80 mg, from about 25 mg to about 75 mg, or from about 40 mg to about 60 mg. In certain embodiments, the concentration of one or more diluents contained in the rapidly dissolving pharmaceutical compositions herein can range from about 0.5% to about 25%, by weight based on the total weight of the rapidly dissolving pharmaceutical composition. In certain embodiments, the concentration of one or more diluents contained in the rapidly dissolving pharmaceutical compositions herein can range from about 0.75% to about 20%, from about 1% to about 15%, from about 3% to about 10%, or from about 5% to about 8%, by weight based on the total weight of the rapidly dissolving pharmaceutical composition.

Because of the low drug load of hydrocodone bitartrate in the rapidly dissolving pharmaceutical compositions herein, the uniformity of dosage units and blend uniformity are a critical tablet property. The method of ingredient addition, including the order of mixing ingredients, can significantly affect tablet blend flow behavior, which can eventually affect blend uniformity and tablet content uniformity.

The initial "lay out" of an active agent, such as hydrocodone bitartrate, within a blend can have a large impact on blender performance as it can affect the overall mixing rate and sometimes lead to inhomogeneous blends. For V-type blenders, since cross-sectional mixing is driven by the faster convective process, mixing rate is significantly enhanced by loading the active agent (or the active agent pre-blend) in an even distribution along this axis of rotation. A loading method, which can be referred to as "sandwiching" or "layering", first places a fraction of the excipients in the blender, then distributes the active agent (or a pre-blend containing the active agent) evenly over the entire surface of excipients, and finally places the remainder of the excipients over the surface of the active agent. Distributing a pre-blend of active agent and excipients into a layer may be simpler than forming a thin uniform layer of pure active agent. The larger volume of material in the pre-blend makes it easier to form an even layer and reduces the risk of a having widely differing active agent concentrations along the axis. Loading methods for active agent also can affect the performance of V-blenders, and especially the active agent mixing rate.

One non-limiting actual example of a "sandwich" layering and blending method for adding and mixing ingredients to form a rapidly dissolving pharmaceutical composition including guaifenesin and hydrocodone bitartrate is as follows:

(a) Screened about 421 mg of a guaifenesin mixture comprising 95% (w/w) guaifenesin, 0.20% (w/w) colloidal silicon dioxide, 3.1% (w/w) maltodextrin, 1.2% (w/w) povidone K-30, and 0.50% (w/w) stearic acid (commercially available as Compresso GGF 95 SA, Granules India Limited 8-2-293/A/A/2, Rd NO. 2, Banjara Hills, India) using a Sweco L518 Sifter equipped with a #18 (980 micron) screen (commercially available from SWECO, a business unit of M-I L.L.C., 8029 Dixie Highway, Florence, Ky. 41042 USA), to form a "Compresso Blend".

(b) Added 50% of about 56.105 mg of microcrystalline cellulose to a V-10 V blender (commercially available from Vanguard Pharmaceutical Machinery, Inc., 21755 Interstate 45 North, Building No. 6, Spring, Tex., U.S.A.). Then added 5 mg of crospovidone, 5 mg of hydrocodone bitartrate, 7.895 mg of stearic acid powder, and 5 mg of talc to the V blender. Next, added the remaining 50% of the 56.105 mg of microcrystalline cellulose to the blender. The mixture was blended for 10 to 15 minutes at 15 rpm to form a hydrocodone mixture, which is transferred to a polybag lined container.
(c) Screened the hydrocodone mixture using the Sweco L518 Sifter equipped with a #30 screen (542 micron);
(d) Screened 5 mg of magnesium stearate using the Sweco LS18 Sifter equipped with a #30 screen (542 micron).
(e) Added 50% of the screened Compresso Blend to the V blender, then added the hydrocodone mixture, and finally, added the remaining Compresso Blend. The blender was sealed and blended for 30 to 45 minutes at 15 rpm.
(f) Added the screened magnesium stearate to the hydrocodone bitartrate and Compresso Blend, and blended for 5 to 7 minutes at 15 rpm to form the rapidly dissolving pharmaceutical composition.
(g) Compressed tablets of the rapidly dissolving pharmaceutical composition using a Manesty Beta Press tablet press (commercially available from Union Standard Equipment, 600 Mamaroneck Ave #400, Harrison, N.Y. 10528 USA) to a target weight of 505 mg for each tablet produced.

The rapidly dissolving pharmaceutical compositions according to the present disclosure provide safe and convenient delivery of the drug substances, remain safe and efficacious after storage, and produce a desired bioavailability of the active agents.

Certain specifications are important to consider in the development of certain dosage forms. For example, the hardness of a tablet is an important consideration to ensure the tablet is suitably resistant to chipping, abrasion, and/or breakage during storage and handling. Tablet hardness testing, is a laboratory technique used by the pharmaceutical industry to test the breaking point and structural integrity of a tablet under conditions of storage, transportation, and handling before usage. The strength of the rapidly dissolving pharmaceutical composition tablets was measured using a tablet hardness tester, such as the Engineering Systems C50 tablet hardness tester, commercially available from Engineering Systems (Nottm) Ltd., Nottingham, England. The hardness of the tablet is the force in Kp (kiloponds) required to break a tablet. The higher the Kp value, the stronger the tablet is.

The friability of a tablet is another important consideration to ensure the tablet can withstand abrasion during packaging, handling, and/or transportation. Friability is often tested using a friabilator apparatus, such as a Guoming CS-2 tablet friability tester, commercially available from Tianjin Guoming Medicinal Equipment Co., Ltd., Tianjin, China. The friabilator apparatus tumbles the dosage forms for a set number of rotations, and the weights of the tablets before and after the tumbling process are compared. Friability is the percentage of the tablet weight loss after a certain number of revolutions in the friabilator. The lower the percentage, the stronger the tablet. For example, friability may be empirically characterized by a percentage, e.g., 1%, that indicates the weight percentage of a compressed dosage form lost during the tumbling test for friability.

Certain embodiments of the rapidly dissolving pharmaceutical composition herein are compressed into tablet dosage forms having a friability of less than 1%. Certain embodiments of the rapidly dissolving pharmaceutical composition are compressed into tablet dosage forms having a friability of less 1.5%, less than 1.25%, less than 0.5%, less than 0.3%, less than 0.15%, less than 0.10%; less than 0.09%, less than 0.08%, less than 0.075%, less than 0.07%, less than 0.06%, or less than 0.05%; from 0.03% to about 0.2%, from about 0.04% to about 0.15%, of from about 0.05% to about 0.1%.

In certain embodiments, the rapidly dissolving pharmaceutical composition herein is compressed into tablet dosage forms having hardness ranging from about 6 Kp (kilopond) to about 12 Kp. In certain embodiments, the rapidly dissolving pharmaceutical composition is compressed into tablet dosage forms having a hardness from about 5 Kp to about 20 Kp, from about 7 Kp to about 17 Kp, or from about 8 Kp to about 16 Kp.

The desired rapidly dissolving pharmaceutical composition exhibits uniformity, via blend uniformity and/or content uniformity, to better ensure that each dosage form comprising the composition contains the desired amounts/concentrations of active drug substances. The uniformity of pharmaceutical compositions mentioned on the context of the invention is meant to be determined as mentioned in the United States Pharmacopeia (USP)<905>. In certain situations, pharmaceutical compositions that contain large amounts of active agents relative to the total mass of the pharmaceutical composition require further optimization to provide adequate uniformity.

The term "uniformity of dosage unit" is defined as the degree of uniformity in the amount of the drug substance among dosage units as defined in USP <905>. As used herein, the term "drug substance" refers to the active pharmaceutical ingredient. The uniformity of each rapidly dissolving pharmaceutical composition can be demonstrated using methods such as content uniformity and weight variation.

As used herein, the phrase "content uniformity" refers to an amount of an individual content of specific drug substance(s) in a number of dosage forms to determine whether the individual content is within a criteria of identified limits set and can be applied in all cases.

In various embodiments of the rapidly dissolving pharmaceutical compositions according to the present disclosure, the content uniformity of hydrocodone bitartrate can range from 75% and 125%. In certain embodiments, the content uniformity of hydrocodone bitartrate in the composition can range from 70% to 130%, from 70% to 120%, from 60% to 110% from 50% to 100%, from 40% to 90%, from 30% to 80% from 20% to 70%, or from 10% to 100%. In various embodiments, the content uniformity of guaifenesin can range from 75% to 125%. In certain embodiments of the compositions herein, the content uniformity of guaifenesin can range from 70% to 130%, from 70% to 120%, from 60% to 110% from 50% to 100%, from 40% to 90%, from 30% to 80% from 20% to 70%, or from 10% to 100%.

As used herein, the phrase "acceptance value" is a calculated value, $AV=|M-X|+ks$, where X is sample mean as percent of label claim (% LC); k is 2.4 for a sample size of 10 units ("L1") and k is 2.0 for a sample size of 30 units ("L2"); s is the standard deviation of the sample; and M depends on the sample mean. If X is between 98.5% LC and 101.5% LC, then M=X. If X is <98.5% LC, then M=98.5. If X is >101.5% LC, then M=101.5.

As used herein, the term "% LC Guaifenesin" refers to the percent label claim of Guaifenesin, a calculated value, % $LC=[R_{sample}/R_{Guaifenesin}]\times[(W_{STD1}\times P)/Std\ DF]\times[(Smp\ DF)/400\ mg]\times 100$, where:

$R_{sample}$=Peak area response of the analyte (Hydrocodone Bitartrate or Guaifenesin) in the Test Solution $R_{HYB}$=Peak area response of the Hydrocodone Bitartrate in the Working Standard Solution $R_{Guaifenesin}$=Peak area response of the Guaifenesin in the Working Standard Solution
$W_S$=Weight of the standard (mg)
P=Potency or Purity of standard (decimal)
Std.DF=Dilution Factor for standard (mL/mL)
Smp.DF=Dilution Factor for sample (mL/mL)
Wt=Weight of blend sample (mg)
5 mg=Label Claim for Hydrocodone Bitartrate
400 mg=Label Claim for Guaifenesin
494.49=Molecular Weight of Hydrocodone Bitartrate Disesquihydrate.
449.46=Molecular Weight of Hydrocodone Bitartrate anhydrous.

As used herein, the term "% LC Hydrocodone Bitartrate" refers to the percent label claim of Hydrocodone Bitartrate, a calculated value, % LC=$[R_{Sample}/R_{HYB}] \times [(W_{STD1} \times P)/\text{Std DF}] \times [(\text{Smp DF})/5 \text{ mg}] \times 100$.

In certain embodiments of the rapidly dissolvable pharmaceutical composition according to the present disclosure, the content uniformity may further have an acceptance value ("AV") of not more than 15.0 at L1. The content uniformity may further have an AV of not more than 25.0 at L2.

As used herein, the phrase "blend uniformity" refers to the degree of uniformity in the amount of the drug substance among a blend of ingredients after 10 minutes of pre-blending at 15 rpm, and 40 minutes of blend time at 15 rpm.

In various embodiments of the rapidly dissolvable pharmaceutical composition according to the present disclosure, the blend uniformity can range from 90% and 110%. In certain embodiments of the compositions, the blend uniformity can range from 80% to 115%, from 85% to 105%, from 90% to 100%, or from 95% to 100%. The standard deviation of the blend uniformity cannot exceed more than 5%. In certain embodiments, the blend uniformity of hydrocodone bitartrate can range from 90% and 110%. In certain embodiments, the blend uniformity of hydrocodone bitartrate can range from 80% to 115%, from 85% to 105%, from 90% to 100%, or from 95% to 100%. The relative standard deviation of the blend uniformity of hydrocodone bitartrate cannot exceed more than 3%. In certain embodiments of the compositions herein, the blend uniformity of guaifenesin can range from 90% and 110%. In certain embodiments, the blend uniformity of guaifenesin can range from 80% to 115%, from 85% to 105%, from 90% to 100%, or from 95% to 100%. The relative standard deviation of the blend uniformity of guaifenesin cannot exceed more than 5%.

In addition to the above, the desired rapidly dissolving pharmaceutical composition must possess adequate dissolution characteristics. Dissolution is an important quality-control test performed on pharmaceutical compositions. In some aspects, the dissolution method is based upon the USP dissolution test procedure for immediate release products as described in USP <711>. The method includes using a Type 2 USP Paddle Apparatus (commercially available at Quality Lab Accessories, LLC, 100 Emlen Way, Suite 108, Telford, Pa. 18969, U.S.A.) at 50 rpm with 900 mL of various dissolution media, including deionized water (pH 7.0), hydrochloric acid (pH 1.2), acetate buffer (pH 4.5), and phosphate buffer (pH 7.5) at about 37° C. The rapidly dissolving pharmaceutical composition is placed into the apparatus and the amount of the active ingredient, i.e., hydrocodone bitartrate or guaifenesin, dissolved in the dissolution medium is measured over various time periods using an HPLC equipped with a pump, autosampler, diode array detector, and data acquisition system.

As shown in the non-limiting examples, the rapidly dissolving pharmaceutical composition may release at least 85% guaifenesin, by weight of the rapidly dissolving pharmaceutical composition, after 15 minutes according to the USP Paddle Method at 50 rpm using a deionized water dissolution medium (pH 7.0) at about 37° C.

In certain embodiments herein, the rapidly dissolving pharmaceutical composition releases at least 85% hydrocodone bitartrate, by weight of the rapidly dissolving pharmaceutical composition, after 15 minutes according to the USP Paddle Method at 50 rpm using a deionized water (pH 7.0) dissolution medium at about 37° C.

In one aspect, the rapidly dissolving pharmaceutical composition releases at least 85% guaifenesin, by weight of the rapidly dissolving pharmaceutical composition, after 15 minutes according to the USP Paddle Method at 50 rpm using a 0.1 N hydrochloric acid (pH 1.2) dissolution medium at about 37° C. The rapidly dissolving pharmaceutical composition releases at least 85% hydrocodone bitartrate, by weight of the rapidly dissolving pharmaceutical composition, after 15 minutes according to the USP Paddle Method at 50 rpm using the 0.1 N hydrochloric acid (pH 1.2) dissolution medium at about 37° C.

In various embodiments, the rapidly dissolving pharmaceutical composition releases at least 85% guaifenesin, by weight of the rapidly dissolving pharmaceutical composition, after 15 minutes according to the USP Paddle Method at 50 rpm using an acetate buffer (pH 4.5) dissolution medium at about 37° C. In certain embodiments, the rapidly dissolving pharmaceutical composition releases at least 85% hydrocodone bitartrate, by weight of the rapidly dissolving pharmaceutical composition, after 15 minutes according to the USP Paddle Method at 50 rpm using the acetate buffer (pH 4.5) dissolution medium at about 37° C.

In various embodiments, the rapidly dissolving pharmaceutical composition releases at least 85% guaifenesin, by weight of the rapidly dissolving pharmaceutical composition, after 15 minutes according to the USP Paddle Method at 50 rpm using a phosphate buffer (pH 7.5) dissolution medium at about 37° C. In certain embodiments, the rapidly dissolving pharmaceutical composition releases at least 85% hydrocodone bitartrate, by weight of the rapidly dissolving pharmaceutical composition, after 15 minutes according to the USP Paddle Method at 50 rpm using the phosphate buffer (pH 7.5) dissolution medium at about 37° C.

The term "$C_{max}$" as used herein refers to the maximum (i.e., peak) serum concentration.

The term "AUC" as used herein refers to the integral of the concentration-time curve.

The term "$AUC_{0 \to t}$" as used herein refer to the area under a plasma concentration versus time curve from time 0 to the time of the last measured concentration of drug within the plasma.

The term "$AUC_{0 \to \infty}$" as used herein refer to the area under a plasma concentration versus time curve from time 0 to infinity.

The term "fasting" and phrases "fasting condition" or "fasting conditions", as used herein, refer to conditions wherein a pharmaceutical composition is administered to a human subject on an empty stomach.

The phrase "fed condition" or "fed conditions", as used herein, refers to conditions wherein a pharmaceutical composition is administered to a human subject following a test meal.

The term "$T_{max}$" as used herein refers to the time after administration of a drug when the maximum plasma concentration is reached.

The term "$t_{1/2}$" as used herein refers to the half-life of an administered drug.

The term "$K_{el}$" as used herein refers to the elimination rate constant which represents the fraction of the drug eliminated per unit of time.

Generally, hydrocodone bitartrate is orally administered as an analgesic and antitussive to adult human subjects in tablet dosages of 5 mg, 7.5 mg, or 10 mg every four to six hours as needed for pain. Similarly, it is generally recommended that guaifenesin, an expectorant, is orally administered every four hours in tablet dosages ranging from 200 mg to 400 mg. The rapidly dissolving pharmaceutical composition may be orally administered to an adult human subject in fasting conditions as a single dose including an about 80:1 weight ratio of guaifenesin to hydrocodone bitartrate. For example, in certain embodiments, the single dose may include about 400 mg of guaifenesin and about 5 mg of hydrocodone bitartrate.

In certain of these embodiments, when orally administered to an adult subject under fasting conditions as a single dose, the rapidly dissolving pharmaceutical composition herein provides a therapeutically effective plasma concentration of guaifenesin with a $C_{max}$ ranging from about 6.89 µg/mL to about 7.57 µg/mL and/or an $AUC_{0 \to t}$ ranging from about 7.47 µg·h/mL to about 8.21 µg·h/mL and/or an $AUC_{0 \to \infty}$ ranging from about 7.47 µg·h/mL to about 8.21 µg·h/mL and/or a $T_{max}$ ranging from about 0.39 h to about 0.89 h and/or a $t_{1/2}$ value ranging from about 0.66 h to about 1.44 h and/or a $K_{el}$ ranging from about 0.44 $h^{-1}$ to about 1.08 $h^{-1}$.

In certain aspects, when orally administered to an adult human subject in fasting conditions as a single dose including an about 80:1 weight ratio of guaifenesin to hydrocodone bitartrate, various embodiments of the rapidly dissolving pharmaceutical composition herein provide a therapeutically effective plasma concentration of guaifenesin with a $C_{max}$ ranging from about 6.89 µg/mL to about 7.57 µg/mL, from about 6.0 µg/mL to about 8.5 µg/mL, from about 6.5 µg/mL to about 8.5 µg/mL, from about 7.0 µg/mL to about 7.8 µg/mL, from about 7.0 µg/mL to about 7.5 µg/mL, or from about 7.2 µg/mL to about 7.7 µg/m L.

In certain aspects, when orally administered to an adult human subject in fasting conditions as a single dose including an about 80:1 weight ratio of guaifenesin to hydrocodone bitartrate, various embodiments of the rapidly dissolving pharmaceutical composition herein provide a therapeutically effective plasma concentration of guaifenesin with an $AUC_{0 \to t}$ ranging from about 6.5 µg·h/mL to about 9.5 µg·h/mL, from about 7.0 µg·h/mL to about 9.0 µg·h/mL, from about 7.2 µg·h/mL to about 8.8 µg·h/mL, from about 7.3 µg·h/mL to about 8.5 µg·h/mL, from about 7.6 µg·h/mL to about 8.3 µg·h/mL, or from about 7.8 µg·h/mL to about 8.0 µg·h/mL.

In certain aspects, when orally administered to an adult human subject in fasting conditions as a single dose of an about 80:1 weight ratio of guaifenesin to hydrocodone bitartrate, various embodiments of the rapidly dissolving pharmaceutical composition herein provide a therapeutically effective plasma concentration of guaifenesin with an $AUC_{0 \to \infty}$ ranging from about 6.5 µg·h/mL to about 9.5 µg·h/mL, from about 7.0 µg·h/mL to about 9.0 µg·h/mL, from about 7.2 µg·h/mL to about 8.8 µg·h/mL, from about 7.3 µg·h/mL to about 8.5 µg·h/mL, from about 7.6 µg·h/mL to about 8.3 µg·h/mL, from about 7.8 µg·h/mL to about 8.0 µg·h/mL, from 5.8 µg·h/mL to about 9.0 µg·h/mL, or from 6.0 µg·h/mL to about 9.3 µg·h/m L.

In certain aspects, when orally administered to an adult human subject in fasting conditions as a single dose including an about 80:1 weight ratio of guaifenesin to hydrocodone bitartrate, various embodiments of the rapidly dissolving pharmaceutical composition herein provide a therapeutically effective plasma concentration of guaifenesin with a $T_{max}$ ranging from about 0.1 h to about 1.5 h, from about 0.2 h to about 1.3 h, from about 0.3 h to about 1.0 h, from about 0.4 h to about 0.9 h, from about 0.3 h to about 0.8 h, or from about 0.5 h to about 0.7 h.

In certain aspects, when orally administered to an adult human subject in fasting conditions as a single dose including an about 80:1 weight ratio of guaifenesin to hydrocodone bitartrate, various embodiments of the rapidly dissolving pharmaceutical composition herein provide a therapeutically effective plasma concentration of guaifenesin with a $t_{1/2}$ ranging from about 0.4 h to about 1.7 h, from about 0.5 h to about 1.6 h, from about 0.6 h to about 1.5 h, from about 0.7 h to about 1.2 h, or from about 0.8 h to about 1.0 h.

In certain aspects, when orally administered to an adult human subject in fasting conditions as a single dose including an about 80:1 weight ratio of guaifenesin to hydrocodone bitartrate, various embodiments of the rapidly dissolving pharmaceutical composition herein provide a therapeutically effective plasma concentration of guaifenesin with a $K_{el}$ ranging from about 0.2 $h^{-1}$ to about 1.5 $h^{-1}$, about 0.3 $h^{-1}$ to about 1.4 $h^{-1}$, about 0.4 $h^{-1}$ to about 1.3 $h^{-1}$, about 0.5 $h^{-1}$ to about 1.5 $h^{-1}$, about 0.6 $h^{-1}$ to about 1.7 $h^{-1}$, or about 0.4 $h^{-1}$ to about 0.95 $h^{-1}$.

In another aspect, when orally administered to an adult human subject in fasting conditions as a single dose including an about 80:1 weight ratio of guaifenesin to hydrocodone bitartrate, various embodiments of the rapidly dissolving pharmaceutical composition herein provide a plasma concentration of hydrocodone bitartrate having a $C_{max}$ ranging from 2.09 µg/mL to about 2.49 µg/mL and/or an $AUC_{0 \to t}$ ranging from about 3.98 µg·h/mL to about 4.44 µg·h/mL and/or an $AUC_{0 \to \infty}$ ranging from about 4.03 µg·h/mL to about 4.51 µg·h/mL and/or a $T_{max}$ ranging from about 0.85 h to about 2.37 h and/or a $t_{1/2}$ ranging from about 4.14 h to about 5.76 h and/or a $K_{el}$ ranging from about 0.11 $h^{-1}$ to about 0.17 $h^{-1}$.

In another aspect, when orally administered to an adult human subject in fasting conditions as a single dose including an about 80:1 weight ratio of guaifenesin to hydrocodone bitartrate, various embodiments of the rapidly dissolving pharmaceutical composition herein provide a plasma concentration of hydrocodone bitartrate having a $C_{max}$ ranging from 2.09 µg/mL to about 2.49 µg/mL, from about 1.0 µg/mL to about 3.5 µg/mL, from about 1.3 µg/mL to about 3.3 µg/mL, from about 1.7 µg/mL to about 3.0 µg/m L, from about 1.85 µg/mL to about 2.7 µg/m L, or from about 2.0 to about 2.2 µg/mL.

In another aspect, when orally administered to an adult human subject in fasting conditions as a single dose including an about 80:1 weight ratio of guaifenesin to hydrocodone bitartrate, various embodiments of the rapidly dissolving pharmaceutical composition herein provide a plasma concentration of hydrocodone bitartrate having an $AUC_{0 \to t}$ ranging from about 3.98 µg·h/mL to about 4.44 µg·h/mL, from about 3.0 µg·h/mL to about 5.5 µg·h/mL, from about 3.3 µg·h/mL to about 5.2 µg·h/mL, from about 3.5 µg·h/mL to about 5.0 µg·h/mL, from about 4.0 µg·h/mL to about 4.5 µg·h/mL, or from about 3.8 µg·h/mL to about 4.2 µg·h/m L.

In another aspect, when orally administered to an adult human subject in fasting conditions as a single dose including an about 80:1 weight ratio of guaifenesin to hydrocodone bitartrate, various embodiments of the rapidly dissolving pharmaceutical composition herein provide a plasma concentration of hydrocodone bitartrate having an $AUC_{0\to\infty}$ ranging from about 4.03 µg·h/mL to about 4.51 µg·h/mL, from about 3.0 µg·h/mL to about 5.4 µg·h/mL, from about 3.5 µg·h/mL to about 5.0 µg·h/mL, from about 4.0 µg·h/mL to about 5.0 µg·h/mL, from about 3.5 µg·h/mL to about 4.5 µg·h/mL, from about 4.2 µg·h/mL to about 4.5 µg·h/mL, or from about 4.3 to about 4.7 µg·h/m L.

In another aspect, when orally administered to an adult human subject in fasting conditions as a single dose including an about 80:1 weight ratio of guaifenesin to hydrocodone bitartrate, various embodiments of the rapidly dissolving pharmaceutical composition herein provide a plasma concentration of hydrocodone bitartrate with a $T_{max}$ ranging from about 0.85 h to about 2.37 h, from about 0.20 h to about 3.5 h, from about 0.4 h to about 3.2 h, from about 0.5 h to about 3.0 h, from about 0.7 h to about 2.5 h, from about 0.75 to about 2.4 h, from about 0.90 h to about 2.2 h, or from about 1.0 h to about 2.0 h.

In another aspect, when orally administered to an adult human subject in fasting conditions as a single dose including an about 80:1 weight ratio of guaifenesin to hydrocodone bitartrate, various embodiments of the rapidly dissolving pharmaceutical composition herein provide a plasma concentration of hydrocodone bitartrate with a $t_{1/2}$ ranging from about 4.14 h to about 5.76 h, from about 3.5 h to about 6.5 h, from about 3.7 h to about 6.3 h, from about 3.9 h to about 6.0 h, from about 4.25 h to about 5.5 h, from about 3.7 h to about 5.8 h, or from about 4.1 h to about 5.85 h.

In another aspect, when orally administered to an adult human subject in fasting conditions as a single dose including an about 80:1 weight ratio of guaifenesin to hydrocodone bitartrate, various embodiments of the rapidly dissolving pharmaceutical composition herein provide a plasma concentration of hydrocodone bitartrate having a $K_{el}$ ranging from about 0.11 $h^{-1}$ to about 0.17 $h^{-1}$, from about 0.01 $h^{-1}$ to about 0.30 $h^{-1}$, from about 0.04 $h^{-1}$ to about 0.20 $h^{-1}$, from about from about 0.08 $h^{-1}$ to about 0.19 $h^{-1}$, from about 0.10 $h^{-1}$ to about 0.16 $h^{-1}$, from about 0.13 $h^{-1}$ to about 0.15 $h^{-1}$, or from about 0.12 $h^{-1}$ to about 0.18 $h^{-1}$.

When orally administered to an adult human subject in fed conditions as a single dose including an about 80:1 weight ratio of guaifenesin to hydrocodone bitartrate, various embodiments of the rapidly dissolving pharmaceutical composition herein provide a therapeutically effective plasma concentration of guaifenesin of $C_{max}$ ranging from about 6.37 µg/mL to about 7.25 µg/mL and/or an $AUC_{0\to t}$ ranging from about 7.42 µg·h/mL to about 8.08 µg·h/mL and/or an $AUC_{0\to\infty}$ ranging from about 7.42 µg·h/mL to about 8.10 µg·h/mL and/or a $T_{max}$ ranging from about 0.70 h to about 1.66 h and/or a $t_{1/2}$ ranging from about 0 h to about 9.09 h and/or a $K_{el}$ ranging from about 0.25 $h^{-1}$ to about 0.97 $h^{-1}$.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a therapeutically effective plasma concentration of guaifenesin with a $C_{max}$ ranging from about 6.37 µg/mL to about 7.25 µg/mL, from about 5.5 µg/mL to about 8.3 µg/mL, from about 5.8 µg/mL to about 8.0 µg/mL, from about 6.0 µg/mL to about 7.5 µg/mL, from about 6.2 µg/mL to about 7.0 µg/mL, or from about 6.4 µg/mL to about 7.5 µg/m L.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a therapeutically effective plasma concentration of guaifenesin having an $AUC_{0\to t}$ ranging from about 7.42 µg·h/mL to about 8.08 µg·h/mL, about 6.0 µg·h/mL to about 8.9 µg·h/mL, about 6.5 µg·h/mL to about 8.8 µg·h/mL, about 6.8 µg·h/mL to about 8.2 µg·h/mL, from about 7.0 µg·h/mL to about 8.5 µg·h/mL, from about 7.4 µg·h/mL to about 9.0 µg·h/mL, or from about 7.7 µg·h/mL to about 8.7 µg·h/mL.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a therapeutically effective plasma concentration of guaifenesin having an $AUC_{0\to\infty}$ ranging from about 7.42 µg·h/mL to about 8.10 µg·h/mL, about 6.0 µg·h/mL to about 8.9 µg·h/mL, about 6.5 µg·h/mL to about 8.8 µg·h/mL, about 6.8 µg·h/mL to about 8.2 µg·h/mL, from about 7.0 µg·h/mL to about 8.5 µg·h/mL, from about 7.4 µg·h/mL to about 9.0 µg·h/mL, or from about 7.7 µg·h/mL to about 8.7 µg·h/mL.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a therapeutically effective plasma concentration of guaifenesin with a $T_{max}$ ranging from about 0.70 h to about 1.66 h, from about 0.40 h to about 2.5 h, from about 0.5 h to about 2.0 h, from about 0.75 h to about 1.75 h, from about 0.65 h to about 1.70 h, or from about 0.8 h to about 1.55 h.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a therapeutically effective plasma concentration of guaifenesin with a $t_{1/2}$ ranging from about 0.0 h to about 9.09 h, from about 0.0 h to about 10 h, from about 0.2 h to about 9.7 h, from about 0.5 h to about 9.5 h, from about 1.0 h to about 9.5 h, from about 3.0 h to about 8.0 h, from about 0.0 h to about 8.0 h, from about 0.0 h to about 7.0 h, from about 0.0 h to about 6.0 h, or from about 0.0 h to about 5.0 h.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a therapeutically effective plasma concentration of guaifenesin having a $K_{el}$ ranging from about 0.25 $h^{-1}$ to about 0.97 $h^{-1}$, from about 0.05 $h^{-1}$.

In to about 1.8 $h^{-1}$, from about 0.1 $h^{-1}$ to about 1.5 $h^{-1}$, from about 0.2 $h^{-1}$ to about 1.0 $h^{-1}$, from about 0.3 $h^{-1}$ to about 1.2 $h^{-1}$, or from about 0.2 $h^{-1}$ to about 0.90 $h^{-1}$.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a plasma concentration of hydrocodone bitartrate having a $C_{max}$ ranging from 2.15 µg/mL to about 2.75 µg/mL and/or with an $AUC_{0\to t}$ ranging from about 4.08 µg·h/mL to about 4.50 µg·h/mL and/or with an $AUC_{0\to\infty}$ ranging from about 4.12 µg·h/mL to about 4.56 µg·h/mL and/or with a $T_{max}$ ranging from about 1.18 h to about 2.98 h and/or with a $t_{1/2}$ ranging from about 4.09 h to about 6.49 h and/or having a $K_{el}$ ranging from about 0.12 $h^{-1}$ to about 0.16 $h^{-1}$.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a plasma concentration of hydrocodone having a $C_{max}$ ranging from about 2.15 µg/mL to about 2.75 µg/mL, from about 1.5 µg/mL to about 3.5 µg/mL, from about 1.9 µg/mL to about 3.0 µg/mL, from about 2.0 µg/mL to about 3.2 µg/mL, from about 2.3 µg/mL to about 2.5 µg/mL, or about 1.9 µg/mL to about 3.0 µg/mL.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a plasma concentration of hydrocodone bitartrate having an $AUC_{0 \to t}$ ranging from about 4.08 µg·h/mL to about 4.50 µg·h/mL, from about 3.0 µg·h/mL to about 5.3 µg·h/mL, from about 3.25 to about 4.3 µg·h/mL, from about 3.8 µg·h/mL to about 4.7 µg·h/mL, from about 4.0 µg·h/mL to about 4.2 µg·h/mL, or from about 4.2 µg·h/mL to about 4.6 µg·h/mL.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a plasma concentration of hydrocodone bitartrate having an $AUC_{0 \to \infty}$ ranging from about 4.12 µg·h/mL to about 4.56 µg·h/mL, from about 3.0 µg·h/mL to about 5.3 µg=h/mL, from about 3.25 to about 4.3 µg·h/mL, from about 3.8 µg·h/mL to about 4.7 µg·h/mL, from about 4.0 µg·h/mL to about 4.2 µg·h/mL, or from about 4.2 µg·h/mL to about 4.6 µg·h/mL.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a plasma concentration of hydrocodone bitartrate with a $T_{max}$ ranging from about 1.18 h to about 2.98 h, from about 0.7 h to about 3.7 h, from about 0.9 h to about 3.4 h, from about 0.8 h to about 3 h, from about 0.95 h to about 2.8 h, or from about 1 to about 3.2 h.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a plasma concentration of hydrocodone bitartrate of $t_{1/2}$ ranging from about 4.09 h to about 6.49 h, from about 2.8 h to about 8 h, from about 3.5 h to about 7.5 h, from about 3.0 h to about 7.0 h, from about 3.6 to about 6.8 h, or from about 3.75 h to about 6.7 h, or from about 4.0 h to about 6.0 h or from about 4.5 h to about 6.6 h.

In certain aspects, when orally administered to an adult human subject in fed conditions as a single dose including an about 80:1 weight ratio of guaifenesin to hydrocodone bitartrate, various embodiments of the rapidly dissolving pharmaceutical composition herein provide a plasma concentration of hydrocodone bitartrate having a $K_{el}$ ranging from about 0.12 $h^{-1}$ to about 0.16 $h^{-1}$, from about 0.01 $h^{-1}$ to about 0.30 $h^{-1}$, from about 0.05 $h^{-1}$ to about 0.2 $h^{-1}$, from about 0.08 $h^{-1}$ to about 0.018 $h^{-1}$, from about 0.10 $h^{-1}$ to about 0.17 $h^{-1}$, or from about 0.13 $h^{-1}$ to about 0.15 $h^{-1}$.

In certain aspects, administering a rapidly dissolving composition comprising guaifenesin and hydrocodone to an adult human who has ingested food within 30 minutes of administration, wherein the rapidly dissolving pharmaceutical composition provides a guaifenesin $AUC_{0 \to \infty}$ ranging from about 7.42 µg*h/mL to about 8.10 µg*h/mL, wherein a remaining concentration of hydrocodone bitartrate is greater than about 90% by weight and a remaining concentration of guaifenesin is greater than about 90% by weight after the rapidly dissolving rapidly dissolving pharmaceutical composition has been stored for at least 6 months at a temperature ranging from 23° C. to 27° C. and a relative humidity ranging from 55% to 65%.

In certain aspects, administering a rapidly dissolving composition comprising guaifenesin and hydrocodone to an adult human who has ingested food within 30 minutes of administration, wherein the rapidly dissolving pharmaceutical composition provides a guaifenesin $AUC0 \to \infty$ ranging from about 7.42 µg*h/mL to about 8.10 µg*h/mL, wherein a remaining concentration of hydrocodone bitartrate is greater than about 90% by weight and a remaining concentration of guaifenesin is greater than about 90% by weight after the rapidly dissolving rapidly dissolving pharmaceutical composition has been stored for at least 1 month at a temperature ranging from 38° C. to 42° C., and a relative humidity ranging from 70% to 80%.

Figure 1B:
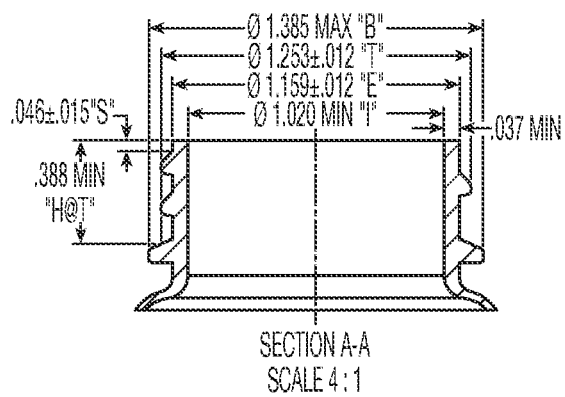
Figure 1C:
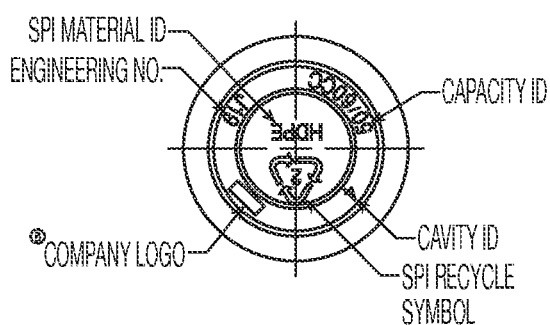
Figure 2A:
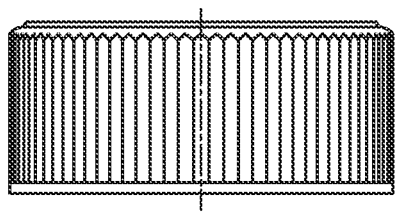
Figure 2B:
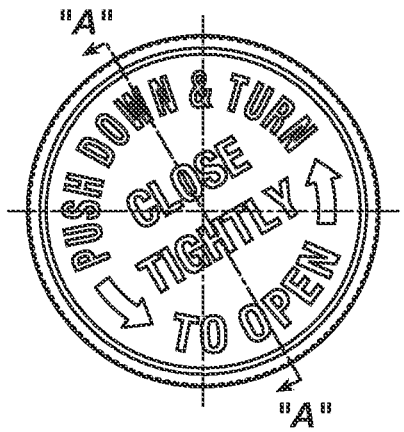
Figure 2C:
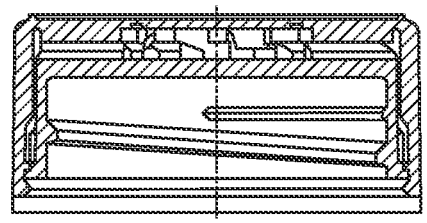

In various non-limiting embodiments, rapidly dissolving pharmaceutical composition tablets according to the present disclosure can be disposed in container closure systems including 50 $cm^3$ to 60 $cm^3$ (30 count), 100 $cm^3$ (100 count), or 400 $cm^3$ (500 count) white high-density polyethylene (HDPE) round containers with, for example, child-resistant container (CRC) closures. For example, a 30 count container closure system can include a white HDPE container made from MARLEX™ HHM 5502BN polyethylene (as illustrated in FIGS. 1A, 1B, and 1C) and a white 33 mm CRC closure (as illustrated in FIGS. 2A, 2B, and 2C). In various embodiments, cotton, for example, Puritan Coil 9 gm 22# (VB) cotton, may be included in the container along with the tablets.

Figure 3:
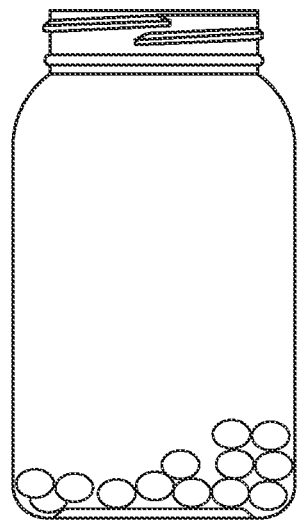
FIG. 3 is a side view of a high density polyethylene container (100 $cm^3$) including a threaded neck used to contain a pharmaceutical composition, as described herein.
Figure 4A:
Figure 4B:
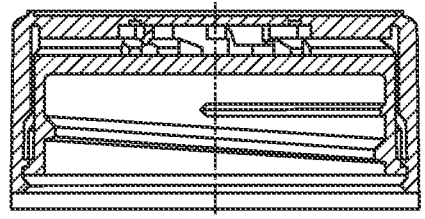

In certain non-limiting embodiments, a 100 count container closure system can include a 100 $cm^3$ HDPE white container (as illustrated in FIG. 3) used in conjunction with a white 38 mm CRC closure (as illustrated in FIGS. 4A and 4B). In various embodiments, cotton, for example, Puritan Coil 9 gm 22# (VB) cotton, may be included in the container with the rapidly dissolving pharmaceutical composition tablets.

Figure 5:
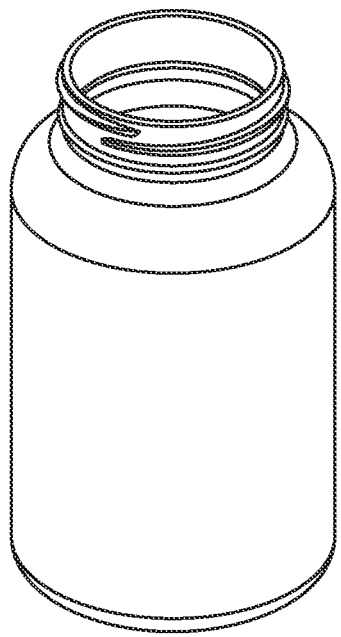
FIG. 5 is an isometric view of a high density polyethylene (HDPE) container (400 $cm^3$) including a threaded neck used to contain a pharmaceutical composition, as described herein.
Figure 6A:
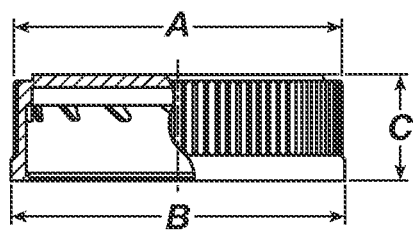
Figure 6B:
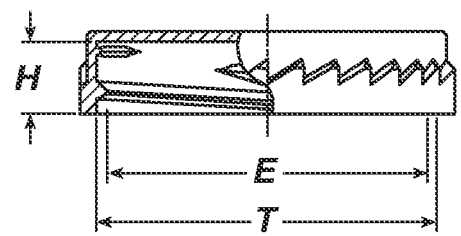

In certain non-limiting embodiments, a 500 count container closure system can include a 400 $cm^3$ HDPE white container (as illustrated in FIG. 5) used in conjunction with a 53 mm CRC white closure (as illustrated in FIGS. 6A and 6B). In various embodiments, cotton, for example, Puritan Coil 9 gm 22# (VB) cotton, may be included in the container with the rapidly dissolving pharmaceutical composition tablets.

EXAMPLES

The examples that follow describe certain non-limiting embodiments, without restricting the scope of the present invention. Persons having ordinary skill in the art will appreciate that variations of the following examples are possible within the scope of the invention, which is defined solely by the claims.

Example 1

The friability, hardness, and uniformity of a rapidly dissolving pharmaceutical composition containing an 80:1 ratio of guaifenesin and hydrocodone bitartrate were evaluated in several studies. Because of the low drug load of hydrocodone bitartrate in the rapidly dissolving pharmaceutical composition, the uniformity of dosage units and blend uniformity were evaluated in a series of studies.

A first series of studies evaluated whether the addition of silicon dioxide, changes in blend time of the mixture, the addition of talc, and changes in mesh size improved uniformity of dosage units and blend uniformity of the rapidly dissolving pharmaceutical composition.

A second series of studies further evaluated whether altering the amounts of several excipients improved uniformity of dosage units and blend uniformity of the rapidly dissolving pharmaceutical composition.

Methods

The formulations in the following examples were prepared as described below. The following process describes the preparation of Formulation 1, the composition of which is shown in Table 1 below.

First, 421 mg of granules of Compresso GGF 95 SA (95% (w/w) guaifenesin, 0.20% (w/w) colloidal silicon dioxide, 3.1% (w/w) maltodextrin, 1.2% (w/w) povidone K-30, and 0.50% (w/w) stearic acid) were screened using a Sweco LS 18 Sifter equipped with a #18 screen (980 micron) to form a screened "Compresso Blend".

Second, a "hydrocodone mixture" was prepared by first adding 25.6 mg microcrystalline cellulose to a V-10 V blender, as described herein. Next, 15 mg of crospovidone, 5 mg of hydrocodone bitartrate, and 7.90 mg of stearic acid powder were added to the blender. Finally, another 25.6 mg of microcrystalline cellulose was added to the blender to form the hydrocodone mixture. The layered ingredients were blended for 10 minutes at 15 rpm, transferred to a new polybag-lined container, and screened using a Sweco LS 18 Sifter (commercially available from Sweco, a business unit of M-I L.L.C., 8029 Dixie Highway, Florence, Ky. 41042) equipped with a #20 screen (864 micron) to form the hydrocodone mixture.

To prepare the final rapidly dissolving pharmaceutical composition mixture, the following ingredients were layered into the V blender. A first half of the Compresso Blend was first added to the V blender, then the entire hydrocodone mixture was added on top of the first half of the Compresso Blend, and finally, the second half of the Compresso Blend was added to the V blender. The V blender was sealed and blended for 40 minutes at 15 rpm to form a final rapidly dissolving pharmaceutical composition mixture. Portions of the mixture were compressed into tablets using a Manesty Beta Press tablet press, with each table having a target weight of 500 mg.

Prior to preparation of the final rapidly dissolving pharmaceutical composition mixture, samples of the Compresso Blend and the hydrocodone mixture were collected to measure blend uniformity using a high-performance liquid chromatography ("HPLC") system, such as a PerkinElmer™ Series 200, HPLC system, commercially available from PerkinElmer, Inc., Melville, N.Y., U.S.A.

In preparation for HPLC analysis, a diluent and reference standards for hydrocodone bitartrate, and for guaifenesin and hydrocodone bitartrate were initially prepared. Diluent for use in the HPLC analysis was prepared by first dissolving approximately 6.8 g of potassium phosphate monobasic in 1000 mL of deionized water. Then, 850 mL of the potassium phosphate aqueous solution was mixed with 150 mL of acetonitrile and 0.2 mL of triethylamine. The mobile phase was also prepared in the same method as used to prepare the diluent.

A standard solution of hydrocodone bitartrate was prepared by first drying a portion of a hydrocodone bitartrate reference standard under vacuum at not less than 15 inches of mercury at 105° C. for 2 hours. In instances where the hydrocodone bitartrate dried reference standard turned yellow during the drying process, the standard was discarded and the standard preparation repeated. The hydrocodone bitartrate dried reference standard was then transferred into a desiccator containing phosphorus pentoxide. 10 mg of the hydrocodone bitartrate dried reference standard was then added to a 100 mL volumetric flask. Approximately 60 mL of diluent was added to the 100 mL volumetric flask containing the dried reference standard and sonicated for 1 minute. Finally, diluent was added to the 100 mL mark to form the standard solution of hydrocodone bitartrate.

A working standard solution of guaifenesin and hydrocodone bitartrate for use in the HPLC analysis also was prepared. First, 40 mg of guaifenesin reference standard was added to a 50 mL volumetric flask. Next, 5 mL of the standard solution of hydrocodone bitartrate was added to the same flask along with 20 mL of diluent. The resulting solution was sonicated for 1 minute, and diluent was then added to the 50 mL mark to form the standard solution of guaifenesin and hydrocodone bitartrate.

Figure 8:
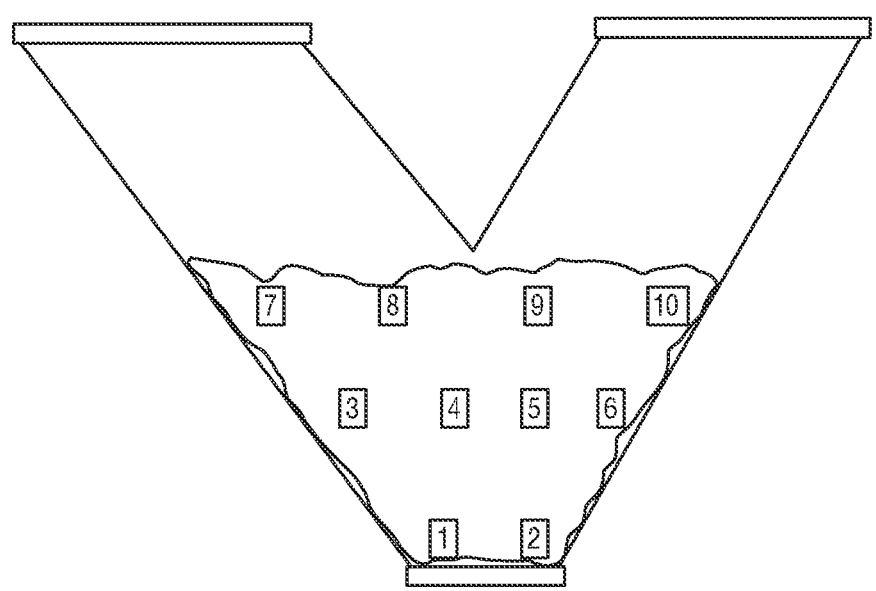
FIG. 8 is a schematic of sampling locations in a V blender to determine blend uniformity of the pharmaceutical composition therein.

Three sets of ten samples were collected from locations 1-10 within the V blender as shown in FIG. 8 for each of the Compresso and hydrocodone mixtures. Each sample was weighed and then placed in a separate 100 mL volumetric flask. Approximately 50 mL of diluent was added to each of the volumetric flasks and sonicated for approximately 15 minutes. These samples were then allowed to equilibrate to room temperature. Diluent was added to the 100 mL mark and then mixed. 5 mL of the diluent solution was added to a clean 50 mL volumetric flask for each of the samples. Diluent was again added to each of the volumetric flasks containing the respective first diluent solution to the 50 mL mark and again mixed to form a respective second diluent solution. From each of the samples, 20 mL of the respective second diluent solution was collected and centrifuged, resulting in a clear filtrate that was collected for analysis.

Equal volumes (20 μL) of the diluent, working standard solution of guaifenesin and hydrocodone bitartrate, and test solution were injected, chromatograms were recorded, and the peak area responses were measured using a high-performance liquid chromatography ("HPLC") system, as described herein. The HPLC system was equipped with a pump, autosampler, diode array detector, and a data acquisition system. The HPLC conditions were as follows: Phenomenex Luna column (5 μm C18(2),100 Å, 250 mm×4.6 mm); Phenomenex security guard cartridge (C18, 4×3.0 mm); flow rate of 1.5 mL/min; column temperature at room temperature; injection volume of 20 μL; detection at 210 nm for hydrocodone bitartrate and 275 nm for guaifenesin; and mobile phase that was prepared as described above.

Figure 7:
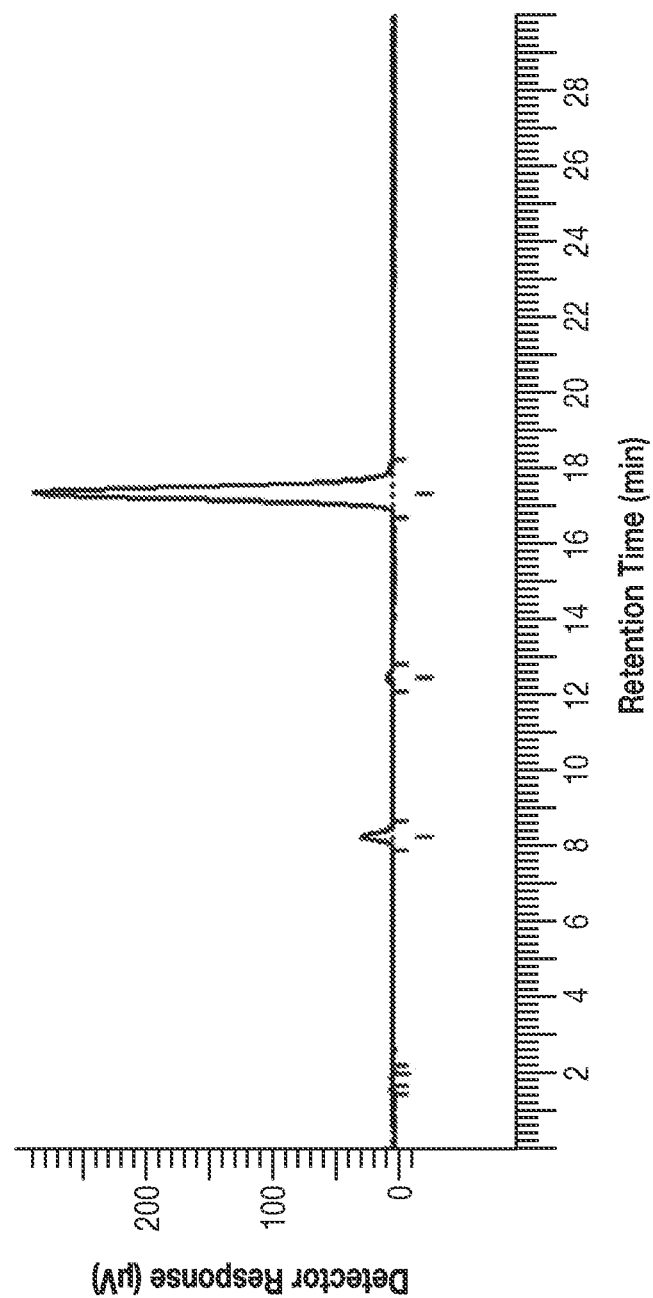
FIG. 7 is a High-Performance Liquid Chromatography (HPLC) chromatogram of an embodiment of a solid dosage form tablet including hydrocodone bitartrate (5 mg) and guaifenesin (400 mg).

To determine the uniformity of dosage units, 10 compressed rapidly dissolving pharmaceutical composition tablets (approx. 500 mg per tablet) were selected. Each tablet was weighed and placed in a separate 50 mL volumetric flask. Diluent and the working standard solution of guaifenesin and hydrocodone bitartrate were prepared in the same method as discussed above for blend uniformity. Diluent was added to the 50 mL mark of each of the volumetric flasks, and each of the volumetric flasks was sonicated for 15 minutes. The contents of each of the volumetric flasks were mixed and allowed to equilibrate to room temperature to form a first diluent solution for each of the 10 samples. 5 mL of the first diluent solution was added to a clean 50 mL volumetric flask for each of the 10 samples. Diluent was again added to each of the volumetric flasks containing the respective first diluent solution to the 50 mL mark and again mixed to form a respective second diluent solution. From each of the 10 samples, 20 mL of the respective second diluent solution was collected and centrifuged, resulting in a clear filtrate that was collected for analysis. These samples were compared to the working standard solution of guaifenesin and hydrocodone bitartrate. Equal volumes of the diluent, working standard solution of guaifenesin and hydrocodone bitartrate, and test solution were injected, chromatograms were recorded, and the peak area responses were measured using HPLC as described above for blend uniformity. FIG. 7 shows the HPLC chromatogram analysis of a test solution of hydrocodone bitartrate 5 mg (see peak at 8.26 min.) and guaifenesin 400 mg solid dosage form tablets (see peak at 17.38 min.). Formulation 2, described in Table 1 below, was prepared using the method described above for Formulation 1. However, 0.20% silicon dioxide, by weight, was additionally added to the V blender when forming the hydrocodone mixture including crospovidone, hydrocodone bitartrate, and stearic acid for Formulation 2. Formulation 2a was prepared using the method described above for Formulation 2. However, the blend time of the final rapidly dissolving pharmaceutical composition mixture for Formulation 2a was reduced from 40 minutes to 30 minutes.

Formulation 3 was prepared using the same method as used to prepare Formulation 2, except that 5 mg of talc (rather than 0.20% silicon dioxide) was added to the V blender when forming the hydrocodone mixture including crospovidone, hydrocodone bitartrate, and stearic acid. Formulation 3a was prepared using the same method as used to prepare Formulation 3, except that the #20 mesh screen used to screen the hydrocodone mixture was replaced with a #30 mesh screen (542 micron).

TABLE 1

Formulation 1, Formulation 2/2a, and Formulation 3/3a.

| | Formulation 1 | | Formulation 2/2a | | Formulation 3/3a | |
|---|---|---|---|---|---|---|
| Ingredient | % (W/V) | mg/tablet | % (W/V) | mg/tablet | % (W/V) | mg/tablet |
| Compresso GGF 95 SA | 84.2 | 421 | 84.2 | 421 | 84.2 | 421 |
| Guaifenesin 95% | | 400 | | 400 | | 400 |
| Colloidal Silicon Dioxide 0.20% | | 0.84 | | 0.84 | | 0.84 |
| Maltodextrin 3.1% | | 13.1 | | 13.1 | | 13.1 |
| Povidone K-30 1.2% | | 5.05 | | 5.05 | | 5.05 |
| Stearic Acid 0.50% | | 2.11 | | 2.11 | | 2.11 |
| Hydrocodone Bitartrate USP | 1.00 | 5.00 | 1.00 | 5.00 | 1.00 | 5.00 |
| Crospovidone, NF | 3.00 | 15.0 | 3.00 | 15.0 | 3.00 | 15.0 |
| Microcrystalline Cellulose PH 102 | 10.2 | 51.11 | 10.2 | 50.9 | 9.22 | 46.1 |
| Stearic Acid Powder | 1.58 | 7.90 | 1.58 | 7.89 | 1.58 | 7.90 |
| Silicon Dioxide, NF | | | 0.03 | 0.158 | | |
| Talc | | | | | 1.00 | 5.00 |
| Total | 100. | 500. | 100. | 500. | 100. | 500. |

In the next series of studies, the levels of talc and crospovidone were varied. The concentration of talc, by weight percent of the composition, was varied in Formulations 3a, 4, and 5, with 1.0% talc used in Formulation 3a, 1.5% talc used in Formulation 4, and 0.5% talc used in Formulation 5. The full compositions for Formulations 4 and 5 are shown below in Table 2. Formulations 4 and 5 were prepared using the same method as for the preparation of Formulation 3a, described above.

TABLE 2

Formulation 4 and Formulation 5.

| | Formulation 4 | | Formulation 5 | |
|---|---|---|---|---|
| Ingredient | % (W/V) | mg/tablet | % (W/V) | mg/tablet |
| Compresso GGF 95 SA | 84.2 | 421 | 84.2 | 421 |
| Guaifenesin 95% | | 400 | | 400 |
| Colloidal Silicon Dioxide 0.20% | | 0.84 | | 0.84 |
| Maltodextrin 3.1% | | 13.1 | | 13.1 |
| Povidone K-30 1.2% | | 5.05 | | 5.05 |
| Stearic Acid 0.50% | | 2.11 | | 2.11 |
| Hydrocodone Bitartrate USP | 1.00 | 5.00 | 1.00 | 5.00 |
| Crospovidone, NF | 3.00 | 15.0 | 3.00 | 15.0 |
| Microcrystalline Cellulose PH 102 | 8.72 | 43.6 | 9.72 | 48.6 |
| Stearic Acid Powder | 1.58 | 7.90 | 1.58 | 7.90 |
| Talc | 1.50 | 7.50 | 0.50 | 2.50 |
| Total | 100 | 500 | 100 | 500 |

As shown in Table 3, below, the level of crospovidone was varied in each of Formulations 6, 7, and 8. For example, the concentration of crospovidone included in the Formulations, by weight percent of the composition, was 3% crospovidone in Formulation 6, 1% in Formulation 7, and 0% in Formulation 8. The full compositions of Formulations 6, 7, and 8 are also shown in Table 3. Formulations 6, 7, and 8 were prepared using the same method as Formulation 3a described above.

As shown in Table 4 above, the addition of silicon dioxide in Formulation 2 did not improve the blend uniformity or uniformity of dosage units of hydrocodone bitartrate relative to Formulation 1. For example, the blend uniformity and uniformity of dosage units of hydrocodone bitartrate for Formulation 2 was 96.0% and 99.3%, respectively, as compared to 96.6% and 100% for the same criteria for Formulation 1 (which did not include silicon dioxide). In contrast, reducing blend time from 40 minutes in Formulation 2 to 30 minutes in Formulation 2a improved the blend uniformity of hydrocodone bitartrate, as shown in Table 4.

TABLE 3

Formulation 6, Formulation 7, and Formulation 8.

| Ingredient | Formulation 6 % (W/V) | Formulation 6 mg/tablet | Formulation 7 % (W/V) | Formulation 7 mg/tablet | Formulation 8 % (W/V) | Formulation 8 mg/tablet |
|---|---|---|---|---|---|---|
| Compresso GGF 95 SA | 84.2 | 421 | 84.2 | 421 | 84.2 | 421 |
| Guaifenesin 95% | | 400 | | 400 | | 400 |
| Colloidal Silicon Dioxide 0.20% | | 0.84 | | 0.84 | | 0.84 |
| Maltodextrin 3.1% | | 13.1 | | 13.1 | | 13.1 |
| Povidone K-30 1.2% | | 5.05 | | 5.05 | | 5.05 |
| Stearic Acid 0.50% | | 2.11 | | 2.11 | | 2.11 |
| Hydrocodone Bitartrate USP | 1.00 | 5.00 | 1.00 | 5.00 | 1.00 | 5.00 |
| Crospovidone, NF | 3.00 | 15.00 | 1.00 | 5.00 | 0.00 | 0.00 |
| Microcrystalline Cellulose PH 102 | 9.22 | 46.1 | 11.2 | 56.1 | 12.2 | 61.1 |
| Stearic Acid Powder | 1.58 | 7.90 | 1.58 | 7.90 | 1.58 | 7.90 |
| Talc | 1.00 | 5.00 | 1.00 | 5.00 | 1.00 | 5.00 |
| Total | 100 | 500 | 100 | 500 | 100 | 500 |

Results

Table 4 below provides a summary of the results of the blend uniformity, uniformity of dosage units, hardness, and friability testing of tablets formed from Formulations 1, 2, 2a, 3, and 3a, which varied in the levels of talc and silicon dioxide, blend time, and screen mesh size.

Table 5, below, provides a summary of the results of varying the concentration of talc in Formulations 3a, 4, and 5 on the blend uniformity, uniformity of dosage units, hardness, and friability of the formed tablets.

TABLE 4

Results of Blend Uniformity, Uniformity of Dosage Units, Average Tablet Hardness, and Friability for Formulations 1, 2, 2a, 3, and 3a.

| Formulation | Blend Uniformity (% LC) Hydrocodone bitartrate | Blend Uniformity (% LC) Guaifenesin | Uniformity of Dosage Units (% LC) Hydrocodone bitartrate | Uniformity of Dosage Units (% LC) Guaifenesin | Average Tablet Hardness (Kp) | Friability (%) |
|---|---|---|---|---|---|---|
| Formulation 1 (no silicon dioxide) | 96.6% LC (RSD 4.2%) | 99.7% LC (RSD 0.7%) | 100% LC (RSD 3.6%) | 98.7% LC (RSD 1.0%) | 13.5-13.7 | 0.07-0.09% |
| Formulation 2 (silicon dioxide) | 96.0% LC (RSD 6.9%) | 99.8% LC (RSD 1.5%) | 99.3% LC (RSD 1.9%) | 99.7% LC (RSD 1.2%) | 13.6-13.8 | 0.04-0.05% |
| Formulation 2a (blend time reduction) | 103% LC (RSD 3.7%) | 97.7% LC (RSD 1.1%) | 98.1% LC (RSD 2.5%) | 98.4% LC (RSD 0.4%) | 13.6-13.8 | 0.09-0.12% |
| Formulation 3 (talc) | 100% LC (RSD 2.7%) | 99.2% LC (RSD 0.5%) | 98.8% LC (RSD 2.5%) | 99.4% LC (RSD 0.6%) | 13.2-13.2 | 0.10-12% |
| Formulation 3a (mesh screen) | 98.3% LC (RSD 3.4%) | 99.4% LC (RSD 0.5%) | 97.9% LC (RSD 1.3%) | 98.0% LC (RSD 0.4%) | 12.1-12.6 | 0.20% |

TABLE 5

Results of Blend Uniformity, Uniformity of Dosage Units, Average Tablet Hardness, and Friability for Formulations 3a, 4, and 5.

| Formulation | Blend Uniformity (% LC) | | Uniformity of Dosage Units (% LC) | | Average Tablet Hardness (Kp) | Friability (%) |
| --- | --- | --- | --- | --- | --- | --- |
| | Hydrocodone bitartrate | Guaifenesin | Hydrocodone bitartrate | Guaifenesin | | |
| Formulation 3a (1% talc) | 98.3% LC (RSD 3.4%) | 99.4% LC (RSD 0.5%) | 97.9% LC (RSD 1.3%) | 98.0% LC (RSD 0.4%) | 12.1-12.6 | 0.20% |
| Formulation 4 (1.5% talc) | 101.5% LC (RSD 2.2%) | 98.0% LC (RSD 0.6%) | 99.6% LC (RSD 1.8%) | 97.7% LC (RSD 0.4%) | 11.3-12.2 | 0.12% |
| Formulation 5 (0.5% talc) | 96.0% LC (RSD 3.1%) | 99.0% LC (RSD 0.8%) | 95.9% LC (RSD 1.1%) | 97.2% LC (RSD 0.4%) | 11.8-12.4 | 0.10% |

Increasing the concentration of talc to 1.5%, by weight, in Formulation 4 from the concentrations in Formulation 3a (1% talc, by weight) and Formulation 5 (0.5% talc, by weight) resulted in a slight improvement in blend uniformity, even though the rapidly dissolving pharmaceutical composition (tablets) were slightly softer. Formulation 5 (0.5% talc, by weight) and Formulation 3a (1% talc, by weight), which both had a decreased talc content as compared to Formulation 4, provided a slight increase in blend uniformity and uniformity of dosage units.

Table 6, below, provides a summary of the results of varying the concentration of crospovidone (0%, 1%, and 3%) on blend uniformity, uniformity of dosage units, and the dissolution data of Formulations 6, 7, and 8.

TABLE 6

Blend Uniformity, Uniformity of Dosage, and Dissolution in water results obtained for Formulations 6, 7, and 8.

| Formulation | Blend Uniformity (% LC) | | Uniformity of Dosage Units (% LC) | | Dissolution at 15 min in water (% LC) | |
| --- | --- | --- | --- | --- | --- | --- |
| | Hydrocodone bitartrate | Guaifenesin | Hydrocodone bitartrate | Guaifenesin | Hydrocodone bitartrate | Guaifenesin |
| Formulation 6 (3% crospovidone) | 95.9% LC (RSD 3.7%) | 98.8% LC (RSD 0.8%) | 96.2% LC (AV = 6.2) | 99.5% LC (AV = 2.5) | 96% LC (RSD 4%) | 97% LC (RSD 1%) |
| Formulation 7 (1% crospovidone) | 94.5% LC (RSD 0.8%) | 99.1% LC (RSD 0.4%) | 97.9% LC (AV = 1.9) | 99.9% LC (AV = 1.2) | 103% LC (RSD 1%) | 96% LC (RSD 2%) |
| Formulation 8 (0% crospovidone) | 95.8% LC (RSD 1.2%) | 99.4% LC (RSD 0.7%) | 96.6% LC (AV = 7.2) | 99.5% LC (AV = 2.4) | 97% LC (RSD 1%) | 95% LC (RSD 0%) |

Table 6 shows that the results obtained using 0%, 1%, and 3% crospovidone, by weight, were similar, varying only by about 1% in blend uniformity and uniformity of dosage units. However, Formulation 7, which included 1% crospovidone, provided increased dissolution in water after a period of 15 minutes, showing 103% LC for hydrocodone bitartrate as compared to 96% LC for hydrocodone bitartrate in Formulation 6 (having 3% crospovidone) and 97% LC for hydrocodone bitartrate in Formulation 8 (without crospovidone). Thus, the inventors observed improved dissolution results for Formulation 7 (including 1% of crospovidone) as compared to Formulations 8 and 9.

Example 2

The uniformity of a rapidly dissolving pharmaceutical composition containing an 80:1 ratio of guaifenesin and hydrocodone bitartrate was evaluated in several scale-up studies. During the scale-up of manufacturing of the rapidly dissolving pharmaceutical composition, it was discovered that filming on the tooling and die table had occurred. Whether the addition of magnesium stearate would improve the formulation was evaluated.

Methods

Formulation 9 was prepared using the following method. First, 50.5 kg of granules of Compresso GGF 95 SA (95% (w/w) guaifenesin, 0.20% (w/w) colloidal silicon dioxide, 3.1% (w/w) maltodextrin, 1.2% (w/w) povidone K-30, and 0.50% (w/w) stearic acid) were screened using a Sweco LS 18 Sifter (as described herein) equipped with a #18 screen (980 micron) to form a screened "Compresso Blend".

Second, an additional mixture of ingredients was prepared to form a "hydrocodone mixture". 50% of 6.73 kg of microcrystalline cellulose (about 3.35 kg) was added to a V-10 V blender (as described herein). Next, 0.600 kg of crospovidone, 0.600 kg of hydrocodone bitartrate, 0.600 kg of talc, and 0.947 kg of stearic acid powder were added to the V blender. Finally, the remaining half of the original 6.73 kg of microcrystalline cellulose was added to the V blender. The ingredients in the V blender were blended for 10 minutes at 15 rpm, transferred to a new, polybag lined container, and screened using a Sweco LS 18 Sifter (as described herein) equipped with a #30 screen (542 micron), providing the hydrocodone mixture.

To prepare a rapidly dissolving pharmaceutical composition mixture, the Compresso Blend and the hydrocodone mixture were layered into the V blender as follows. First, 50% of the Compresso Blend was added to the V blender.

Next, the entire hydrocodone mixture was added to the V blender on top of the first half of the Compresso Blend. Finally, the remaining 50% of the Compresso Blend was added to the V blender. The V blender was sealed, and the ingredients were blended for 30 minutes at 15 rpm.

Next, 0.600 kg of magnesium stearate was pre-screened through a #30 mesh screen. The screened magnesium stearate was added to the blended hydrocodone and Compresso mixtures in the V blender and blended for five minutes at 15 rpm to form the rapidly dissolving pharmaceutical composition mixture. The rapidly dissolving pharmaceutical composition mixture was then compressed into tablets using a Manesty Beta Press tablet press (as described herein), with each tablet having a target weight of 500 mg.

Formulation 10 was prepared using the scale-up method described for Formulation 9, except that the rapidly dissolving pharmaceutical composition did not include stearic acid and contained an increased concentration of 1.5% (wt/wt) talc as compared to 1.0% (wt/wt) talc in Formulation 9.

The compositions of Formulations 9 and 10 are shown below in Table 7.

TABLE 7

Compositions of Formulation 9 and Formulation 10.

| Ingredient | Formulation 9 % (W/V) | Formulation 9 mg/tablet | Formulation 10 % (W/V) | Formulation 10 mg/tablet |
|---|---|---|---|---|
| Compresso GGF 95 SA | 83.4 | 421 | 84.2 | 421 |
| Guaifenesin 95% | | 400 | | 400 |
| Colloidal Silicon Dioxide 0.20% | | 0.84 | | 0.84 |
| Maltodextrin 3.1% | | 13.1 | | 13.1 |
| Povidone K-30 1.2% | | 5.05 | | 5.05 |
| Stearic Acid 0.50% | | 2.11 | | 2.11 |
| Hydrocodone Bitartrate USP | 0.99 | 5.00 | 1.00 | 5.00 |
| Crospovidone, NF | 0.99 | 5.00 | 1.00 | 5.00 |
| Microcrystalline Cellulose PH 102 | 11.1 | 56.1 | 11.3 | 56.5 |
| Stearic Acid Powder, NF | 1.56 | 7.90 | 0.00 | 0.00 |
| Talc, USP | 0.99 | 5.00 | 1.50 | 7.50 |
| Magnesium Stearate, NF | 0.99 | 5.00 | 1.00 | 5.00 |
| Total | 100 | 505 | 100 | 500 |

Results

Table 8, below, provides a summary of the blend uniformity, uniformity of dosage units, and dissolution test results obtained for Formulation 9.

TABLE 8

Blend uniformity, Uniformity of Dosage Units, and Dissolution in water results obtained for Formulation 9.

| Formulation | Blend Uniformity (% LC) Hydrocodone bitartrate | Blend Uniformity (% LC) Guaifenesin | Uniformity of Dosage Units (% LC) Hydrocodone bitartrate | Uniformity of Dosage Units (% LC) Guaifenesin | Dissolution at 15 min in water (% LC) Hydrocodone bitartrate | Dissolution at 15 min in water (% LC) Guaifenesin |
|---|---|---|---|---|---|---|
| Formulation 9 | 96.4% LC (RSD 2.9%) | 101% LC (RSD 0.7%) | 99% LC AV = 5.9 | 98.6% LC AV = 1.4 | 94% LC (RSD 3%) | 89% LC (RSD 3%) |
| Formulation 10 | 98.1% LC | 102% LC | N/A | N/A | N/A | N/A |

Blend uniformity of Formulation 10 (without stearic acid, and with an increased talc content) showed slight improvement as compared to Formulation 9. For example, Formulation 10 had an average blend uniformity of 98.1% for hydrocodone bitartrate as compared to only 96.4% average blend uniformity for Formulation 9. Similarly, the average blend uniformity for guaifenesin in Formulation 10 was increased to 102% as compared to 101% for guaifenesin.

Formulation 9 exhibited desirable filming properties while maintaining adequate uniformity, dissolution, and physical characteristics. For example, as shown in Table 8 above, blend uniformity for Formulation 9 was 96.4% LC for hydrocodone bitartrate and 101% LC for guaifenesin, while the uniformity of dosage units for hydrocodone bitartrate was determined to have an acceptance value of 5.9 for hydrocodone bitartrate and 1.4 for guaifenesin. Physical characteristic analysis resulted in a hardness of the Formulation 9 tablets containing 5 mg of hydrocodone bitartrate and 400 mg of guaifenesin ranging from about 6 Kp to about 12 Kp, a friability of +5%, and a weight variation of no more than 1.0%. Additionally, no visible tablet sticking or tooling and die tablet filming buildup from the dosage form tablets was observed.

Based on previous formulation trials, a single lubricant did not give optimized powder and tablet characteristics. The inventors discovered that using higher concentrations of a single lubricant to get desired product properties could negatively impact tablet characteristics. Thus, instead of using a single lubricant at high concentrations, a combination of boundary lubricants was used. For example, the inventors included a combination of magnesium stearate, stearic acid, and hydrous magnesium silicate or talc in Formulations 9 and 10. Using the three lubricants simultaneously provided excellent powder flow characteristics, enhancing blend and content uniformity, and resulted in good tablet characteristics, with no tablet sticking or blend filming on the tooling and die table during tablet compression. For example, the blend uniformity for Formulation 9 which included three lubricants (i.e., stearic acid, talc, and magnesium stearate) of 96.4% LC for hydrocodone bitartrate and 101% LC for guaifenesin exceeded that of Formulation 7, which included two lubricants (i.e., stearic acid and talc) with blend uniformity values of 94.5% LC for hydrocodone bitartrate and 99.1% for guaifenesin. Moreover, the present inventors surprisingly and unexpectedly observed that the simultaneous use of three lubricants in Formulation 9 promoted free release and less sticking to the tooling and die table as compared to either of Formulation 1 (including one lubricant) or Formulation 7 (including two lubricants).

Example 3

Blend homogeneity is generally dependent on multiple factors including particle size, size distribution, and density of the individual components, blending process or blending equipment, and presence of agglomerates within the blend. Segregation refers to the separation of the coarse from fine material during the flow of a powder or the vibration of a bed of powder. Segregation is the opposite effect to mixing and can occur by several different mechanisms, depending on the particle's physical characteristics and the handling method. Low dose drug formulations require milling/micronisation to increase the number of particles of drugs which could be blended with other excipients and increase homogeneity in the formulation as well as in the final dosage form. The rapidly dissolving pharmaceutical composition formulations are designed by various techniques to obtain granules, agglomerates, or ordered mixtures to avoid segregation and handling issues. In an analysis of whether drug particle size or mixing is accountable for poor content uniformity, it was noted that decreasing particle size enhanced content uniformity, provided drug aggregation is controlled.

Accordingly, because of the low drug load of hydrocodone bitartrate in Formulation 9 and the relative particle size, there was a risk to the blend and content uniformity of the final rapidly dissolving pharmaceutical composition. To mitigate the risk to blend and content uniformity, screening steps were introduced during the blending process.

Methods

Formulation 9 was prepared using the manufacturing method of Example 2, as described herein. After the materials were blended, three sets of ten blend samples were collected from ten locations in the V blender, as illustrated in FIG. 8. The collected samples were analyzed to determine blend uniformity in the same way as described previously. Prior to compression of the rapidly dissolving pharmaceutical composition, samples of the final Compresso (Guaifenesin) and hydrocodone mixtures were collected to measure blend uniformity. Three sets of ten samples were collected from locations 1-10, as shown in FIG. 8, for each of the Compresso (Guaifenesin) and hydrocodone mixtures. During the compression process, ten tablets from the beginning, ten tablets from the middle, and ten tablets from the end from each of Lot Nos. ED12-1, EE12-1, EK12-1, and EJ14-3 were collected, and samples were analyzed to determine content uniformity.

The blend uniformity and content uniformity results for the four lots are shown in Table 9 below.

TABLE 9

Blend Uniformity and Content Uniformity results for Formulation 9 tablets of the rapidly dissolving pharmaceutical composition.

| Lot | Blend Uniformity (% LC) | | Content Uniformity (% LC) | |
|---|---|---|---|---|
| | Hydrocodone bitartrate | Guaifenesin | Hydrocodone bitartrate | Guaifenesin |
| ED12-1 | 102.4% LC (RSD 3.2%) | 99.7% LC (RSD 0.7%) | 100.4% LC (RSD 2.1%) | 99.5% LC (RSD 1.3%) |
| EE12-1 | 100.1% LC (RSD 1.4%) | 99.8% LC (RSD 0.5%) | 100.4% LC (RSD 2.1%) | 99.4% LC (RSD 0.7%) |
| EK12-1 | 103.8% LC (RSD 2.2%) | 100.2% LC (RSD 0.8%) | 103.9% LC (RSD 4.0%) | 98.2% LC (RSD 1.0%) |
| EJ14-3 | 102.3% LC (RSD 1.7%) | 100.0% LC (RSD 0.4%) | 100.6% LC (RSD 1.8%) | 98.8% LC (RSD 1.5%) |

As shown in Table 9, blend uniformity and content uniformity results for the four lots of tablets (each including 5 mg hydrocodone bitartrate and 400 mg guaifenesin per tablet) were similar, and no significant differences between the blending and compression stages of lot production were observed. To characterize the friability of the Formulation 9 tablets (each tablet including 5 mg hydrocodone bitartrate and 400 mg guaifenesin), a 6.5 g sample of the Formulation 9 tablets was dedusted prior to testing and accurately weighed. The dedusted Formulation 9 tablets were then placed in the drum of a friabilator apparatus, such as a Guoming CS-2 friabilator. The friabilator drum was rotated 100 times before removing the tablets. Following removal from the friabilator, the tablets were again dedusted and accurately weighed to determine the friability of the Formulation 9 tablets.

Table 10 below summarizes the characterization results for the final formulation of Example 3, Formulation 9.

TABLE 10

Characterization results of Formulation 9.

| Parameter | | Value |
|---|---|---|
| Blend Uniformity | Hydrocodone bitartrate | 90.0-110.0% (RSD ≤ 3.0%) |
| | Guaifenesin | 90.0-110.0% (RSD ≤ 3.0%) |
| Content Uniformity | Hydrocodone bitartrate | 75.0-125.0% (AV = NMT 15.0) |
| | Guaifenesin | 75.0-125.0% (AV = NMT 25.0) |
| Hardness | | 6.0-12.0 Kp |
| Friability | | NMT 1.0% in 100 revolutions |
| Thickness | | 0.230-0.260 in |
| Weight | | 505.0 mg ± 3.0% |

Example 4

Stability studies were conducted on tablets of the rapidly dissolving pharmaceutical composition containing an 80:1 ratio of guaifenesin and hydrocodone bitartrate stored in a container closure system.

Thirty tablets of rapidly dissolving pharmaceutical composition including 400 mg guaifenesin and 5 mg hydrocodone bitartrate per tablet were stored in a container closure system including a 50/60 $cm^3$ HDPE, white round container (illustrated in FIGS. 1A, 1B, and 1C) with a 33 mm, CRC white closure (illustrated in FIGS. 2A, 2B, and 2C). 9 grams of 22# (VB) Carolina absorbent cotton (commercially available from Carolina Absorbent Cotton Products, a division of Barnhardt Manufacturing Company, 1100 Hawthorne Lane, Charlotte, N.C. 28205, U.S.A.) was included with the tablets in the container.

To package the rapidly dissolving pharmaceutical composition tablets in the container closure system, the HDPE containers initially were blown out with air, evacuated in a vacuum, and visually inspected for any visible particulate matter. Next, a tablet counter, King Electronic Tablet Counter Model TB4 (commercially available from C. E. King, Ltd., 3000 Hillswood Drive, Chertsey, Surrey, United Kingdom) was adjusted and used to fill 30 tablets into each container, and a cotton inserter was used to insert a cotton coil into the tablet-filled containers. Next, a capper apparatus, Swan-Matic Hand Held Electric Capper Model C530 (commercially available from Automation Devices, Inc., 7050 West Ridge Road, Fairview, Pa., U.S.A.) was adjusted (using empty containers and caps) to fit the size of the container and container closure (caps) for appropriate tightening of the caps onto the containers. Once adjusted, the capper apparatus was used to properly cap and tighten a container closure onto each tablet-filled container. Next, an induction seal unit, Portable Cap Induction Sealer, Model CS+Junior (commercially available from Lepel Corporation, W227 N937 Westmound Drive, Waukesha, Wis., U.S.A.) was used to heat seal a safety/tamper evident seal onto each capped container. The induction seal unit, was used at a power setting of 75% percent for 1 to 2 seconds. Finally, the induction sealed, capped, tablet-filled containers were re-torqued using the hand held electric capper to a target removal torque range as verified by a torque tester, Secure Pak Electronic Torque Tester, Model 50-1251IMARCI (commercially available from Secure Pak, a division of Glassline Corporation, 3630 Rockland Circle, Millbury, Ohio, U.S.A.).

Two stability studies were conducted on the rapidly dissolving pharmaceutical composition tablets stored in the container closure system. The stability studies performed in this Example 4 involved the following testing periods and conditions:

Thirty-six months under long term conditions (25° C.±2° C. and 60%±5% relative humidity).

Six months under accelerated conditions (40° C.±2° C. and 75%±5% relative humidity).

The long-term stability study of the rapidly dissolving pharmaceutical composition, conducted over a period of 36 months, was conducted to determine the rate of physical or chemical degradation of the rapidly dissolving pharmaceutical composition (in tablets including 400 mg guaifenesin and 5 mg hydrocodone bitartrate).

All long-term stability samples (each sample containing 400 mg guaifenesin and 5 mg hydrocodone bitartrate, bulk lot ED12-1) were placed upright and maintained in an upright position during the stability study. All of the containers were maintained at 25° C.±2° C. and 60%±5% relative humidity conditions, uninterrupted, (except for the adding or withdrawal of test samples) for a period of 36 months. Samples were removed from conditions at the specified time point and tested for hydrocodone bitartrate content, guaifenesin content, related substances, and dissolution at the required time point using HPLC as described herein.

Shelf life of the formulation was estimated to be at least 36 months at ambient conditions, based upon the long-term (36 months) stability assay results shown in Table 11, which is shown below. The stability study showed greater than 98% of the hydrocodone bitartrate and greater than 98% of the guaifenesin was retained in the pharmaceutical formulation over the course of the long-term stability assay for 36 months.

Table 11 reports the long-term stability data for the table pharmaceutical composition, including 400 mg guaifenesin and 5 mg hydrocodone bitartrate.

TABLE 11

Long-term conditions stability data results for the tablet pharmaceutical composition, including 400 mg guaifenesin and 5 mg hydrocodone bitartrate, at 25° C. ± 2° C. and 60% ± 5% relative humidity over 36 months.

| Test | Specification | T = 0 | T = 3 | T = 6 | T = 9 | T = 12 | T = 18 | T = 24 | T = 36 |
|---|---|---|---|---|---|---|---|---|---|
| Assay | hydrocodone bitartrate | 101% | 98.9% | 100% | 99.5% | 99.5% | 99.6% | 98.4% | 98.6% |
|  | guaifenesin | 103% | 99.0% | 98.7% | 99.0 % | 99.8% | 99.9% | 101 % | 98.5% |
| Dissolution | hydrocodone bitartrate | Avg: 101% Range: 99%-113% | Avg: 108% Range: 104%-111% | Avg: 102% Range: 99%-104% | Avg: 96% Range: 94%-98% | Avg: 102% Range: 100%-105% | Avg: 102% Range: 100%-104% | Avg: 100% Range: 98%-102% | Avg: 100% Range: 97%-103% |
|  | guaifenesin | Avg: 100% Range: 97%-102% | Avg: 100% Range: 99%-102% | Avg: 96% Range: 94%-101% | Avg: 100% Range: 99%-101% | Avg: 100% Range: 99%-101% | Avg: 100% Range: 97%-101% | Avg: 100% Range: 98%-101% | Avg: 101% Range: 99%-102% |
| Related Substances | hydrocodone diol | 0.07% | ND | 0.02% | 0.06% | ND | ND | ND | ND |
|  | dihydrocodeine bitartrate | 0.10% | 0.15% | 0.06% | 0.17% | 0.19% | 0.04% | 0.24% | 0.32% |
|  | guaifenesin β-isomer | 0.29% | 0.29% | 0.29% | 0.30% | 0.29% | 0.28% | 0.30% | 0.29% |
|  | guaiacol | ND | ND | ND | ND | ND | ND | ND | ND |
|  | unspecified | <0.05% | <0.05% | <0.05% | <0.05% | <0.05% | <0.05% | 0.06% | <0.05% |
|  | total (excluding known impurities) | <0.05% | <0.05% | <0.05% | <0.05% | <0.05% | <0.05% | 0.1% | <0.05% |

ND None Detected

An accelerated stability study of the tablet pharmaceutical composition from the same bulk lot (bulk lot ED12-1) as used in the long-term stability study described above (and contained in the closure system) was conducted over a period of six months to determine the rate of physical or chemical degradation of the tablet rapidly dissolving pharmaceutical composition, including 400 mg guaifenesin and 5 mg hydrocodone bitartrate, over accelerated environmental conditions.

All accelerated stability samples (each sample containing 400 mg guaifenesin and 5 mg hydrocodone bitartrate, bulk lot ED12-1) were placed upright and maintained in an upright position during the stability study. All of the containers were maintained at 40° C.±2° C. and 75%±5% relative humidity, uninterrupted, (except for the adding or withdrawal of test samples) for a period of six months. Samples were removed from conditions at the specified time point and tested for hydrocodone bitartrate content, guaifenesin content, related substances, and dissolution at the required time point using HPLC as described herein.

Shelf life of the 400 mg guaifenesin and 5 mg hydrocodone bitartrate pharmaceutical formulation was estimated at approximately six months at the accelerated stability conditions, based upon the accelerated stability assay results shown in Table 12 shown below. The stability study showed greater than 98% of the hydrocodone bitartrate and greater than 99% of the guaifenesin was retained in the tablet rapidly dissolving pharmaceutical composition over the course of the accelerated term stability assay for six months.

Table 12 reports the accelerated stability data for the pharmaceutical formulation, including 400 mg guaifenesin and 5 mg hydrocodone bitartrate per tablet.

collection of blood samples from all the subjects at each time point, samples were centrifuged at 4000 RPM for 10 minutes at 5° C. All plasma samples were then transferred into three polypropylene tubes. The plasma samples were stored at −20±10° C. for a maximum period of 12.0 hours.

TABLE 12

Accelerated conditions stability data results for the rapidly dissolving pharmaceutical composition, including 400 mg guaifenesin and 5 mg hydrocodone bitartrate at 40° C. ±2° C. and 75% ± 5% relative humidity over a period of six months.

| | | Time (months) | | | | |
|---|---|---|---|---|---|---|
| Test | Specification | T = 0 | T = 1 | T = 2 | T = 3 | T = 6 |
| Assay | hydrocodone bitartrate | 101% | 97.8% | 97.3% | 98.1% | 99.2% |
| | guaifenesin | 103% | 101% | 99.2% | 101% | 102% |
| Dissolution | hydrocodone bitartrate | Average: 101% Range: 99%-113% | Average: 96% Range: 93%-100% | Average: 105% Range: 104%-108% | Average: 107% Range: 104%-110% | Average: 102% Range: 99%-105% |
| | guaifenesin | Average: 100% Range: 97%-102% | Average: 97% Range: 93%-101% | Average: 100% Range: 97%-102% | Average: 100% Range: 99%-102% | Average: 97% Range: 94%-101% |
| Related Substances | hydrocodone diol | 0.07% | 0.06% | ND | ND | ND |
| | dihydrocodeine bitartrate | 0.10% | 0.03% | 0.11% | 0.20% | 0.19% |
| | guaifenesin β-isomer | 0.29% | 0.30% | 0.29% | 0.29% | 0.29% |
| | guaiacol | ND | ND | ND | ND | ND |
| | unspecified | <0.05% | <0.05% | <0.05% | <0.05% | <0.05% |
| | total (excluding known impurities) | <0.05% | <0.05% | <0.05% | <0.05% | <0.05% |

ND None Detected

Example 5

A randomized, open-label, balanced, two-treatment, two-period, two sequence, single-dose, two-way crossover oral food effect study was conducted comparing administration of rapidly dissolving pharmaceutical composition tablets including 5 mg hydrocodone bitartrate and 400 mg guaifenesin per tablet to healthy subjects under fed and fasting conditions. The objective of this study was to evaluate the effect of food (high fat, high calorie breakfast) on the rate and extent of absorption of a single oral dose of the rapidly dissolving pharmaceutical composition including 5 mg hydrocodone bitartrate and 400 mg guaifenesin.

Methods

Healthy adult participants were randomized into Treatment A or Treatment B during two study periods (Period 1 and Period 2). Participants received one tablet of the rapidly dissolving pharmaceutical composition (including 5 mg hydrocodone bitartrate and 400 mg guaifenesin per tablet) in each study period with a seven-day (washout) interval between study periods. Participants randomized to Treatment A consumed a high fat, high calorie breakfast (1000 kcal) 30 minutes prior to dosing. Participants randomized to Treatment B fasted overnight and at the time of dosing. Participants were housed at the investigative site not less than 10.5 hours pre-dose until 24 hours post-dose in each period.

Twenty-one blood samples were collected from each subject during each study period. The venous blood samples (9 mL each) were drawn at pre-dose [(0.00) within 1.00 hour prior to dosing] and at 0.16, 0.33, 0.50, 0.66, 0.83, 1.00, 1.25, 1.50, 2.00, 3.00, 4.00, 5.00, 6.00, 7.00, 8.00, 10.00, 12.00, 16.00, 20.00 and 24.00 hours post-dose. After the To demonstrate bioequivalence, certain limits were set, depending on the nature of the drug, patient population, and clinical end-points. It is generally accepted that the 90% confidence interval for the ratio of averages of logarithmically transformed AUC and $C_{max}$ should lie within the range of 80% to 125%. Thus, to demonstrate bioequivalence, the 90% confidence intervals were completely contained within the predefined bioequivalence criteria of 80% to 125% for the primary end points of $C_{max}$ and AUC.

Results

Pharmacokinetic parameters were measured for fed and fasting conditions of subjects for both hydrocodone bitartrate and guaifenesin. Plasma samples were assayed for hydrocodone and guaifenesin using an API 4000® LC-MS/MS System, commercially available from AB Sciex LP, Concord, Ontario, Canada. During analysis, standard and quality control samples were distributed throughout each batch of study samples analyzed. No access to the randomization schedule was available until all of the analysis was completed. All the values below the limit of quantification (LOQ) were set to "zero" for all pharmacokinetic and statistical calculations. Any missing sample was reported as "M". Incurred sample reanalysis was performed as per the current version of ICON SOP BC06, "Incurred Sample Reanalysis Procedures".

The pharmacokinetic parameters for hydrocodone and guaifenesin in plasma were computed using SAS™ v9.3 software, commercially available from SAS Institute, Inc., Cary, N.C., USA.

The plasma pharmacokinetic parameters were determined for $C_{max}$, $T_{max}$, $AUC_{0 \to t}$, and $AUC_{0 \to \infty}$. The $C_{max}$ and $T_{max}$ values were directly determined from the plasma concentration versus time curves. The $AUC_{0 \to t}$ was calculated by the linear trapezoidal rule. The $AUC_{0 \to \infty}$ was estimated by summing the area from $AUC_{0 \to t}$ and $AUC_{0 \to \infty}$. The half life, $t_{1/2}$, was calculated using the formula $t_{1/2}=\ln 2/K_{el}$, wherein $K_{el}$ is the slope of the terminal portion of the plasma concentration versus time curve, obtained by linear regression. Natural Logarithmic transformation was done before data analysis for $C_{max}$, $AUC_{0 \to t}$, and $AUC_{0 \to \infty}$. $T_{max}$, $t_{1/2}$, and $K_{el}$ were analyzed without transformation.

A paired t-test was used to assess effects between the two arms of the study. Intra-subject variability in terms of the overall percentage coefficient of variation (% CV) were also evaluated for each PK parameter. For the pharmacokinetic parameters $C_{max}$, $AUC_{0 \to t}$, and $AUC_{0 \to \infty}$, 90% confidence intervals for the ratios of fed and fasting conditions were calculated from the ln-transformed data. The product was tested for bioequivalence using ratios of the natural Log transformed pharmacokinetic parameters $C_{max}$, $AUC_{0 \to t}$, and $AUC_{0 \to \infty}$, and the respective 90% confidence intervals. All values below the limit of quantification (LOQ) were set to "zero" for all pharmacokinetic and statistical calculations.

Tables 13 and 14, below, summarize the pharmacokinetic parameters for administration of a tablet of the rapidly dissolving pharmaceutical composition (including 5 mg hydrocodone bitartrate and 400 mg guaifenesin per tablet) to subjects under fed and fasting conditions.

As shown in Table 13, the mean $C_{max}$ value of guaifenesin under fasting conditions was 7.23 µg/mL, which is significantly higher than that of guaifenesin (6.81 µg/mL) under fed conditions (p=0.005). The mean $T_{max}$ of guaifenesin under fasting conditions was 0.64 hours, which is significantly shorter than that of guaifenesin (1.18 hours) under fed conditions (p=0.0009). Therefore, in the study of Example 5, guaifenesin reached a higher maximum plasma concentration in a shorter time under fasting conditions than under fed conditions.

Results for the extent of absorption of guaifenesin, as determined from mean $AUC_{0 \to t}$ and $AUC_{0 \to \infty}$ values, were 7.75 and 7.76 µg·h/mL, respectively, under fed conditions, and 7.84 and 7.84 µg·h/mL, respectively, under fasting conditions.

Table 14 shows that the mean $C_{max}$ value of hydrocodone bitartrate under fasting conditions was 2.29 µg/mL, which is lower than that of hydrocodone bitartrate (2.35 µg/mL) under fed conditions (p=0.20). The mean $T_{max}$ of hydrocodone bitartrate under fasting conditions was 1.61 hours, which is significantly shorter than that of hydrocodone bitartrate (2.08 hours) under fed conditions (p=0.09). Therefore, in the study of Example 5, hydrocodone bitartrate reached a similar maximum plasma concentration in a shorter time under fasting conditions than under fed conditions.

Tables 15 and 16, below, report the 90% confidence intervals of the ratios (fed versus fasting conditions) for the natural log (ln)-transformed pharmacokinetic parameters as determined for 400 mg guaifenesin and 5 mg hydrocodone bitartrate.

TABLE 13

Summary of Pharmacokinetic Parameters of Guaifenesin in Subjects Under Treatment A (Fed Condition) and Treatment B (Fasting Condition)*

| PK Parameter | Fed Condition | | | | Fasting Condition | | | | p-value |
|---|---|---|---|---|---|---|---|---|---|
| | Mean | SD | % CV | 90% CI | Mean | SD | % CV | 90% CI | |
| *$C_{max}$ (µg/mL) | 6.81 | 0.44 | 6.39 | 6.60-7.03 | 7.23 | 0.34 | 4.67 | 7.07-7.40 | 0.0005 |
| *$AUC_{0 \to t}$ (µg·h/mL) | 7.75 | 0.33 | 4.32 | 7.58-7.91 | 7.84 | 0.37 | 4.73 | 7.65-8.02 | 0.34 |
| *$AUC_{0 \to \infty}$ (µg·h/mL) | 7.76 | 0.34 | 4.44 | 7.59-7.93 | 7.84 | 0.37 | 4.73 | 7.66-8.03 | 0.43 |
| $T_{max}$ (h) | 1.18 | 0.48 | 40.9 | 0.94-1.42 | 0.64 | 0.25 | 39.76 | 0.51-0.76 | 0.0009 |
| $t_{1/2}$ (h) | 3.36 | 5.73 | 171 | 0.52-6.19 | 1.05 | 0.39 | 36.87 | 0.86-1.24 | 0.18 |
| $K_{el}$ (h$^{-1}$) | 0.61 | 0.36 | 59.25 | 0.43-0.79 | 0.76 | 0.32 | 41.49 | 0.61-0.92 | 0.25 |

*For the natural log (ln)-transformed (ln-transformed)

TABLE 14

Summary of Pharmacokinetic Parameters of Hydrocodone bitartrate in Subjects Under Treatment A (Fed Condition) and Treatment B (Fasting Condition)*

| PK Parameter | Fed Condition | | | | Fasting Condition | | | | p-value |
|---|---|---|---|---|---|---|---|---|---|
| | Mean | SD | % CV | 90% CI | Mean | SD | % CV | 90% CI | |
| *$C_{max}$ (µg/mL) | 2.35 | 0.20 | 8.54 | 2.25-2.45 | 2.29 | 0.20 | 8.58 | 2.19-2.38 | 0.20 |
| *$AUC_{0 \to t}$ (µg·h/mL) | 4.29 | 0.21 | 4.97 | 4.18-4.39 | 4.21 | 0.23 | 5.37 | 4.10-4.35 | 0.052 |
| *$AUC_{0 \to \infty}$ (µg·h/mL) | 4.34 | 0.22 | 5.10 | 4.23-4.45 | 4.27 | 0.24 | 5.58 | 4.15-4.39 | 0.08 |
| $T_{max}$ (h) | 2.08 | 0.90 | 43.51 | 1.63-2.52 | 1.61 | 0.76 | 47.02 | 1.23-1.98 | 0.09 |
| $t_{1/2}$ (h) | 5.29 | 1.20 | 22.66 | 4.69-5.88 | 4.95 | 0.81 | 16.29 | 4.55-5.35 | 0.46 |
| $K_{el}$ (h$^{-1}$) | 0.14 | 0.02 | 17.47 | 0.12-0.15 | 0.14 | 0.03 | 19.00 | 0.13-0.16 | 0.49 |

*For the natural log (ln)-transformed (ln-transformed)

TABLE 15

The 90% Confidence Interval for the Ratio of the Natural Log (ln)-Transformed Data of Guaifenesin Pharmacokinetic Parameters Comparing Results of Subjects Undergoing Treatment A (Fed Conditions) or Treatment B (Fasting Conditions).

| | Ratio Between Treatment A: Treatment B | | | |
|---|---|---|---|---|
| PK Parameter | Mean | SD | Lower Confidence Limit | Upper Confidence Limit |
| *$C_{max}$ (μg/mL) | 0.94 | 0.06 | 0.91 | 0.97 |
| *$AUC_{0 \to t}$ (μg · h/mL) | 0.99 | 0.04 | 0.97 | 1.01 |
| *$AUC_{0 \to \infty}$ (μg · h/mL) | 0.99 | 0.04 | 0.97 | 1.01 |
| $T_{max}$ (h) | 2.15 | 1.25 | 1.53 | 2.76 |
| $t_{1/2}$ (h) | 3.96 | 7.08 | 0.46 | 7.47 |
| $K_{el}$ (h$^{-1}$) | 0.90 | 0.54 | 0.64 | 1.17 |

*For the natural log (ln)-transformed (ln-transformed)

TABLE 16

The 90% Confidence Interval for the Ratio of the Natural Log (ln)-Transformed Data of Hydrocodone Bitartrate Pharmacokinetic Parameters Comparing Results of Subjects Undergoing Treatment A (Fed Conditions) or Treatment B (Fasting Conditions).

| | Ratio Between Treatment A: Treatment B | | | |
|---|---|---|---|---|
| PK Parameter | Mean | SD | Lower Confidence Limit | Upper Confidence Limit |
| *$C_{max}$ (μg/mL) | 1.03 | 0.07 | 0.99 | 1.06 |
| *$AUC_{0 \to t}$ (μg · h/mL) | 1.02 | 0.03 | 1.00 | 1.03 |
| *$AUC_{0 \to \infty}$ (μg · h/mL) | 1.02 | 0.03 | 1.00 | 1.03 |
| $T_{max}$ (h) | 1.51 | 0.83 | 1.09 | 1.92 |
| $t_{1/2}$ (h) | 1.11 | 0.35 | 0.94 | 1.28 |
| $K_{el}$ (h$^{-1}$) | 0.98 | 0.28 | 0.84 | 1.12 |

*For the natural log (ln)-transformed (ln-transformed)

As shown above in Tables 13 and 15, guaifenesin was shown to reach a higher maximum plasma concentration in a shorter period under fasting conditions than under fed conditions. The shorter period for reaching the maximum plasma concentration of guaifenesin can be explained by a lower volume of plasma available under fasting conditions than under fed conditions. Under fed conditions consumption of volumes of water and food before administration of the rapidly dissolving pharmaceutical composition can decrease the concentration of each active ingredient present in the plasma.

As shown above in Tables 14 and 16, the pharmacokinetic parameters for hydrocodone bitartrate ($C_{max}$, $AUC_{0 \to t}$, $AUC_{0 \to \infty}$, $T_{max}$, $t_{1/2}$, and $K_{el}$) were similar under both fed and fasting conditions. As reported in Table 16, the 90% confidence intervals of the ratio of the natural log (ln) transformed pharmacokinetic parameters of hydrocodone bitartrate for the ratio of fed conditions to fasting conditions for $C_{max}$, $AUC_{0 \to t}$, and $AUC_{0 \to \infty}$ were 99% to 106%, 100% to 103%, and 100% to 103%, respectively.

In conclusion, the results of the pharmacokinetic parameter analysis suggested that the hydrocodone and guaifenesin in the rapidly dissolving pharmaceutical composition tablets administered under the fed (high fat, high calorie breakfast) and fasting conditions were bioequivalent. Hydrocodone and guaifenesin under the fasting and fed conditions were similar in pharmacokinetic characteristics among the healthy adult human subjects. Thus, the pharmacokinetic parameter analysis results indicated that hydrocodone and guaifenesin were well tolerated under both conditions.

Example 6

The objective of Example 6 was to compare the rate and extent of absorption of hydrocodone bitartrate and guaifenesin for the rapidly dissolving pharmaceutical composition tablets (including 5 mg hydrocodone bitartrate and 400 mg guaifenesin per tablet) as compared to two other drug tablets. A randomized, open-label, balanced, three-treatment, three-period, three-sequence, single-dose, crossover comparative oral bioavailability study on the following samples was conducted in healthy, adult human subjects:

(1) a tablet of the rapidly dissolving pharmaceutical composition (including 5 mg hydrocodone bitartrate and 400 mg guaifenesin);
(2) a tablet including 5 mg hydrocodone bitartrate and 1.5 mg homatropine, currently commercially available under the trademark TUSSIGON™ and
(3) an over-the-counter 400 mg guaifenesin tablet.

Methods

Each subject received each of the three tablets listed above in a randomized order with a (washout) interval of seven days between each dosing period. The dosing arms used were as follows:

Treatment 1: a tablet of the rapidly dissolving pharmaceutical composition (including 5 mg hydrocodone bitartrate and 400 mg guaifenesin);

Treatment 2: a tablet including 5 mg hydrocodone bitartrate and 1.5 mg homatropine, currently commercially available under the trademark TUSSIGON™ and Treatment 3: an over-the-counter 400 mg guaifenesin tablet.

The sequences of subjects in each of the three study arms were randomized. After drug tablet administration, serial blood samples were collected over a period of 24 hours. Twenty-one blood samples were collected from each subject during each 24 hour period. The venous blood samples (8 mL each) were drawn at pre-dose [(0.00) within 1.00 hour prior to dosing] and at 0.16, 0.33, 0.50, 0.66, 0.83, 1.00, 1.25, 1.50, 2.00, 3.00, 4.00, 5.00, 6.00, 7.00, 8.00, 10.00, 12.00, 16.00, 20.00 and 24.00 hours post dose.

Post-plasma concentrations of hydrocodone bitartrate and guaifenesin were measured by pre-validated LC-MS/MS methods as described herein. PK parameters $C_{max}$, $T_{max}$, $t_{1/2}$, $AUC_{0 \to t}$, $AUC_{0 \to \infty}$, and $K_{el}$ were determined for the hydrocodone bitartrate and guaifenesin, respectively. $C_{max}$, $AUC_{0 \to t}$, and $AUC_{0 \to \infty}$ were used to test for bioequivalence after natural log-transformation of plasma data was completed.

The objective of this study was to evaluate whether the tablet administered in Treatment 1 was considered bioequivalent to the tablets administered in Treatments 2 and 3, in terms of guaifenesin. Bioequivalence was determined where the 90% confidence interval of the natural log-transformed ratios of $C_{max}$, $AUC_{0 \to t}$, and $AUC_{0 \to \infty}$ were within the predetermined bioequivalence range of 80% to 125% (as described herein).

Results

Pharmacokinetic parameters for hydrocodone bitartrate determined from subjects undergoing Treatments 1 and 2 are summarized in Table 17 below.

TABLE 17

Summary of Pharmacokinetic Parameters of Hydrocodone Bitartrate
obtained for Treatment 1 (Hydrocodone Bitartrate,
5 mg, and Guaifenesin, 400 mg) and Treatment 2
(Hydrocodone Bitartrate, 5 mg, and Homatropine, 1.5 mg)*

| PK Parameter | Treatment 1 | | | | Treatment 2 | | | | p-value |
|---|---|---|---|---|---|---|---|---|---|
| | Mean | SD | % CV | 90% CI | Mean | SD | % CV | 90% CI | |
| *$C_{max}$ (µg/mL) | 2.38 | 0.27 | 11.3 | 2.25-2.52 | 2.37 | 0.21 | 8.82 | 2.27-2.48 | 0.84 |
| *$AUC_{0 \to t}$ (µg · h/mL) | 4.24 | 0.23 | 5.44 | 4.13-4.36 | 4.26 | 0.20 | 4.73 | 4.16-4.36 | 0.57 |
| *$AUC_{0 \to \infty}$ (µg · h/mL) | 4.31 | 0.25 | 5.70 | 4.19-4.43 | 4.32 | 0.21 | 4.84 | 4.22-4.42 | 0.65 |
| $T_{max}$ (h) | 1.60 | 1.38 | 86.7 | 0.91-2.28 | 1.28 | 0.57 | 44.5 | 1.00-1.56 | 0.42 |
| $t_{1/2}$ (h) | 5.45 | 1.45 | 26.6 | 4.73-6.17 | 5.67 | 1.42 | 25.1 | 4.96-6.37 | 0.69 |
| $K_{el}$ (h$^{-1}$) | 0.13 | 0.03 | 25.2 | 0.12-0.15 | 0.13 | 0.03 | 25.5 | 0.11-0.15 | 0.68 |

*For the natural log (ln)-transformed (ln-transformed)

As shown in Table 17, the mean $C_{max}$ values of hydrocodone bitartrate of Treatment 1 and Treatment 2 were 2.38 and 2.37 µg/mL, respectively. The mean $T_{max}$ values were 1.6 and 1.28 hours, respectively. The $C_{max}$ and $T_{max}$ determined for hydrocodone bitartrate of Treatment 1 were comparable to those of Treatment 2 with p-values of 0.84 and 0.42, respectively. Results for the extent of absorption were determined from mean $AUC_{0 \to t}$ and $AUC_{0 \to \infty}$ values, as 4.24 and 4.31 µg·h/mL, respectively, in Treatment 1, and 4.26 and 4.32 µg·h/mL, respectively, in Treatment 2. The $AUC_{0 \to t}$ and $AUC_{0 \to \infty}$ values of hydrocodone bitartrate in Treatment 1 were comparable to those in Treatment 2 with p-values of 0.57 and 0.65, respectively. No period or sequence effects were observed for any pharmacokinetic parameters determined for hydrocodone bitartrate from subjects undergoing Treatments 1 and 2.

Pharmacokinetic parameters for guaifenesin determined from subjects undergoing Treatments 1 and 3 are summarized in Table 18 below.

As shown in Table 18, the mean $C_{max}$ values of guaifenesin of Treatment 1 and Treatment 3 were 7.41 and 7.51 µg/mL, respectively. The mean $T_{max}$ values were 0.61 and 0.57 hours, respectively. The $C_{max}$ and $T_{max}$ of guaifenesin of Treatment 1 were comparable to those of Treatment 3 with p-values of 0.26 and 0.34, respectively. Results for the extent of absorption, as determined from mean $AUC_{0 \to t}$ and $AUC_{0 \to \infty}$ values, were 7.93 and 7.94 µg·h/mL, respectively, in Treatment 1, and 7.96 and 7.97 µg·h/mL, respectively, in Treatment 3. The $AUC_{0 \to t}$ and $AUC_{0 \to \infty}$ values of guaifenesin in Treatment 1 were comparable to those in Treatment 3 with p-values of 0.49 and 0.52, respectively. No period or sequence effects were observed for any pharmacokinetic property of guaifenesin.

Results of $C_{max}$, $AUC_{0 \to t}$, and $AUC_{0 \to \infty}$ used to test for bioequivalence after natural log-transformation of plasma data for hydrocodone bitartrate from subjects undergoing treatments 1 and 2 are summarized below in Table 19.

TABLE 18

Summary of Pharmacokinetic Parameters of Guaifenesin obtained for
Treatment 1 (Hydrocodone Bitartrate, 5 mg, and Guaifenesin, 400 mg) and Treatment 3
(Guaifenesin, 400 mg)*

| PK Parameter | Treatment 1 | | | | Treatment 3 | | | | p-value |
|---|---|---|---|---|---|---|---|---|---|
| | Mean | SD | % CV | 90% CI | Mean | SD | % CV | 90% CI | |
| *$C_{max}$ (µg/mL) | 7.41 | 0.59 | 7.92 | 7.12-7.70 | 7.51 | 0.51 | 6.77 | 7.26-7.76 | 0.26 |
| *$AUC_{0 \to t}$ (µg · h/mL) | 7.93 | 0.47 | 5.97 | 7.70-8.17 | 7.96 | 0.50 | 6.22 | 7.72-8.21 | 0.49 |
| *$AUC_{0 \to \infty}$ (µg · h/mL) | 7.94 | 0.47 | 5.94 | 7.71-8.17 | 7.97 | 0.49 | 6.21 | 7.72-8.21 | 0.52 |
| $T_{max}$ (h) | 0.61 | 0.17 | 28.0 | 0.53-0.70 | 0.57 | 0.14 | 25.2 | 0.50-0.65 | 0.34 |
| $t_{1/2}$ (h) | 1.13 | 0.25 | 21.8 | 1.10-1.26 | 1.12 | 0.69 | 61.8 | 0.78-1.46 | 0.94 |
| $K_{el}$ (h$^{-1}$) | 0.64 | 0.15 | 23.4 | 0.57-0.71 | 0.73 | 0.23 | 31.5 | 0.62-0.85 | 0.24 |

*For the natural log (ln)-transformed (ln-transformed)

TABLE 19

The 90% Confidence Interval for the Ratio of the Natural Log (ln)-Transformed Data of Hydrocodone Bitartrate Comparing Treatment 1 (Hydrocodone Bitartrate, 5 mg, and Guaifenesin, 400 mg) and Treatment 2 (Hydrocodone Bitartrate, 5 mg, and Homatropine, 1.5 mg)

| | Ratio Between Treatment 1:Treatment 2 | | | |
|---|---|---|---|---|
| PK Parameter | Mean | SD | Lower Confidence Limit | Upper Confidence Limit |
| *$C_{max}$ (µg/mL) | 1.00 | 0.06 | 0.97 | 1.03 |
| *$AUC_{0 \to t}$ (µg · h/mL) | 1.00 | 0.02 | 0.99 | 1.01 |
| *$AUC_{0 \to \infty}$ (µg · h/mL) | 1.00 | 0.02 | 0.99 | 1.01 |
| $T_{max}$ (h) | 1.32 | 0.88 | 0.89 | 1.76 |
| $t_{1/2}$ (h) | 1.01 | 0.33 | 0.85 | 1.18 |
| $K_{el}$ (h$^{-1}$) | 1.10 | 0.38 | 0.91 | 1.29 |

*For the natural log (ln)-transformed (ln-transformed)

As shown in Table 19, the 90% confidence intervals for the ratios of $C_{max}$, $AUC_{0 \to t}$, and $AUC_{0 \to \infty}$ of hydrocodone bitartrate were determined as 97% to 103%, 99% to 101%, and 99% to 101%, respectively, meeting the predetermined criteria for bioequivalence of 80% to 125%. The mean $t_{1/2}$ was 5.45 hours in Treatment 1 and 5.67 hours in Treatment 2, suggesting no significant difference between the two treatments (p=0.69). There was also no significant difference (p=0.68) between the $K_{el}$ of Treatment 1 (0.13 h$^{-1}$) and that of Treatment 2 (0.13 h$^{-1}$).

The mean values and 90% confidence intervals of Treatment 1 and Treatment 2 ratios for these parameters were as follows: $C_{max}$, 2.38 versus 2.37 µg/mL (97% to 103%); $AUC_{0 \to t}$, 4.24 versus 4.26 µg·h/mL (99% to 101%); and $AUC_{0 \to \infty}$, 4.31 versus 4.32 µg·h/mL (99% to 101%).

Results of $C_{max}$, $AUC_{0 \to t}$, and $AUC_{0 \to \infty}$ used to test for bioequivalence after natural log-transformation of plasma data for hydrocodone bitartrate are summarized below in Table 20.

TABLE 20

The 90% Confidence Interval for the Ratio of the Natural Log (ln)-Transformed Data of Hydrocodone Bitartrate Comparing Treatment 1 (Hydrocodone Bitartrate, 5 mg, and Guaifenesin, 400 mg) and Treatment 3 (Guaifenesin, 400 mg)

| | Ratio Between Treatment 1:Treatment 3 | | | |
|---|---|---|---|---|
| PK Parameter | Mean | SD | Lower Confidence Limit | Upper Confidence Limit |
| *$C_{max}$ (µg/mL) | 0.99 | 0.04 | 0.97 | 1.01 |
| *$AUC_{0 \to t}$ (µg · h/mL) | 1.00 | 0.02 | 0.99 | 1.01 |
| *$AUC_{0 \to \infty}$ (µg · h/mL) | 1.00 | 0.02 | 0.99 | 1.01 |
| $T_{max}$ (h) | 1.09 | 0.27 | 0.96 | 1.22 |
| $t_{1/2}$ (h) | 1.17 | 0.34 | 1.00 | 1.34 |
| $K_{el}$ (h$^{-1}$) | 1.01 | 0.66 | 0.69 | 1.34 |

*For the natural log (ln)-transformed (ln-transformed)

As shown in Table 20, the mean values and 90% confidence intervals of Treatment 1 and Treatment 3 ratios for the pharmacokinetic parameters (see Table 18) of interest in bioequivalence determination were as follows: $C_{max}$, 7.41 versus 7.51 µg/mL (97% to 101%); $AUC_{0 \to t}$, 7.93 versus 7.96 µg·h/mL (99% to 101%); and $AUC_{0 \to \infty}$, 7.94 versus 7.97 µg·h/mL (99% to 101%). Thus, the 90% confidence intervals for the ratios of natural long (ln) transformed data of treatments 1 and 3 (see Table 20) for $C_{max}$, $AUC_{0 \to t}$, and $AUC_{0 \to \infty}$ were 97% to 101%, 99% to 101%, and 99% to 101%, respectively, meeting the predetermined criteria for bioequivalence of 80% to 125% for each parameter. The mean $t_{1/2}$ was 1.13 hours in Treatment 1 and 1.12 hours in Treatment 3, suggesting no significant difference between the two treatments (p=0.94). There was also no significant difference (p=0.24) between the $K_{el}$ of Treatment 1 (0.64 h$^{-1}$) and that of Treatment 2 (0.73 h$^{-1}$).

No significant difference was found based on a paired t-test for any pharmacokinetic parameters of guaifenesin between the rapidly dissolving pharmaceutical composition tablet (including 5 mg hydrocodone bitartrate and 400 mg guaifenesin) and the over-the-counter 400 mg guaifenesin tablet.

Results from the PK analyses suggest that under fasting conditions, the rapidly dissolving pharmaceutical composition tablet is bioequivalent to the TUSSIGON™ tablet in terms of hydrocodone bitartrate. Additionally the analyses also suggest that under fasting conditions, the rapidly dissolving pharmaceutical composition tablet is bioequivalent to the over-the-counter guaifenesin 400 mg tablet in terms of guaifenesin.

Example 7

A dissolution study of a rapidly dissolving pharmaceutical composition tablet (including 5 mg hydrocodone bitartrate and 400 mg guaifenesin) was performed to compare the release profile with that of an over-the-counter tablet including 5 mg hydrocodone bitartrate and 1.5 mg homatropine, currently commercially available under the trademark TUSSIGON™, and an over-the-counter 400 mg guaifenesin tablet.

Methods

The dissolution profiles of the rapidly dissolving pharmaceutical composition tablets including hydrocodone bitartrate and guaifenesin (Lot #EJ14-3), hydrocodone bitartrate and homatropine methylbromide tablets, and guaifenesin tablets were performed in four media of varying pH. The dissolution profile method parameters used for testing the three samples are shown in Table 21 below.

TABLE 21

Dissolution profile method parameters used for dissolution testing of hydrocodone bitartrate and guaifenesin tablets of rapidly dissolving pharmaceutical composition (Lot # EJ14-3), hydrocodone bitartrate and homatropine methylbromide tablets, and guaifenesin tablets.

| | |
|---|---|
| Dissolution Mediums | Deionized water |
| | 0.1N Hydrochloric Acid (pH 1.2) |
| | Acetate Buffer (pH 4.5) |
| | Phosphate Buffer (pH 7.5) |
| Volume | 900 mL |
| Apparatus | USP Type II Apparatus (Paddles) |
| Speed | 50 RPM |
| Temperature | 37.0° C. ± 0.5° C. |
| Time Points | 5, 10, 15, 30, 45, 60 minutes |
| Acceptance Criteria | NLT 85% at 15 minutes |

Specifications for the dissolution acceptance criteria were established based on average in vitro dissolution data for each lot under study, equivalent to USP <711> Dissolution Apparatus 2-Paddle-Stage 2 testing (n=2), which is hereby incorporated by reference.

Results

The dissolution profiles for both hydrocodone bitartrate and guaifenesin in a rapidly dissolving pharmaceutical composition tablet (Lot #EJ14-3) are summarized in Tables 22 and 23 below for each of the dissolution media.

TABLE 22

Percent Dissolved Hydrocodone Bitartrate (Hydrocodone Bitartrate, 5 mg, and Guaifenesin, 400 mg, in one rapidly dissolving pharmaceutical composition tablet of Lot # EJ14-3) at Varied pH Values.

| Medium | N | 5 min | 10 min | 15 min | 30 min | 45 min | 60 min |
|---|---|---|---|---|---|---|---|
| Deionized Water (pH 7.0) | Mean | 60 | 90 | 96 | 100 | 101 | 101 |
| | % RSD | 9.6% | 5.0% | 3.2% | 1.5% | 1.2% | 1.4% |
| 0.1N HCl (pH 1.2) | Mean | 76 | 101 | 108 | 110 | 111 | 111 |
| | % RSD | 15.9% | 4.6% | 2.2% | 1.8% | 1.7% | 1.5% |
| Acetate Buffer (pH 4.5) | Mean | 63 | 97 | 105 | 109 | 110 | 111 |
| | % RSD | 13.7% | 4.2% | 2.9% | 1.8% | 1.6% | 1.5% |
| Phosphate Buffer (pH 7.5) | Mean | 53 | 94 | 103 | 109 | 113 | 113 |
| | % RSD | 9.7% | 7.7% | 4.1% | 2.5% | 2.0% | 2.0% |

TABLE 23

Percent Dissolved Guaifenesin (Hydrocodone Bitartrate, 5 mg, and Guaifenesin, 400 mg, in one rapidly dissolving pharmaceutical composition tablet of Lot # EJ14-3) at Varied pH Values.

| Medium | N | 5 min | 10 min | 15 min | 30 min | 45 min | 60 min |
|---|---|---|---|---|---|---|---|
| Deionized Water (pH 7.0) | Mean | 61 | 88 | 93 | 97 | 98 | 98 |
| | % RSD | 7.8% | 4.8% | 3.4% | 2.3% | 2.0% | 1.7% |
| 0.1N HCl (pH 1.2) | Mean | 70 | 92 | 98 | 99 | 100 | 100 |
| | % RSD | 14.2% | 4.6% | 2.5% | 1.7% | 1.3% | 1.2% |
| Acetate Buffer (pH 4.5) | Mean | 59 | 88 | 94 | 98 | 99 | 99 |
| | % RSD | 12.3% | 3.6% | 2.4% | 1.7% | 1.3% | 1.0% |
| Phosphate Buffer (pH 7.5) | Mean | 47 | 81 | 88 | 94 | 96 | 98 |
| | % RSD | 10.0% | 7.7% | 4.3% | 2.7% | 1.9% | 1.6% |

Based on the data shown in Tables 22 and 23, in vitro release of hydrocodone bitartrate and guaifenesin showed similar results in all media at varied pH values. After 15 minutes, more than 85% of hydrocodone bitartrate and guaifenesin were dissolved in all media at the various pH values shown in Tables 22 and 23.

The dissolution profile for the TUSSIGON™ tablet including hydrocodone bitartrate and homatropine methylbromide tablet is summarized below in Table 24 for each of the media used for evaluation.

TABLE 24

Dissolution Profile of Hydrocodone Bitartrate, 5 mg, and Homatropine Methylbromide, 1.5 mg, at Varied pH Values.

| Medium | N | 5 min | 10 min | 15 min | 30 min | 45 min | 60 min |
|---|---|---|---|---|---|---|---|
| Deionized Water (pH 7.0) | Mean | 94 | 100 | 102 | 103 | 104 | 104 |
| | % RSD | 6.0% | 3.3% | 2.5% | 2.3% | 1.9% | 2.1% |
| 0.1N HCl (pH 1.2) | Mean | 101 | 110 | 111 | 112 | 113 | 113 |
| | % RSD | 6.8% | 2.1% | 1.7% | 1.1% | 0.8% | 0.8% |
| Acetate Buffer (pH 4.5) | Mean | 103 | 109 | 111 | 112 | 112 | 113 |
| | % RSD | 6.3% | 2.5% | 2.0% | 1.5% | 1.6% | 1.3% |
| Phosphate Buffer (pH 7.5) | Mean | 98 | 108 | 110 | 112 | 113 | 114 |
| | % RSD | 13.7% | 3.2% | 2.0% | 1.5% | 1.1% | 1.5% |

The dissolution profile for guaifenesin tablet is summarized in Table 25 for each of the media used for evaluation.

TABLE 25

Dissolution Profile of Guaifenesin, 400 mg, at Varied pH Values.

| Medium | N | 5 min | 10 min | 15 min | 30 min | 45 min | 60 min |
|---|---|---|---|---|---|---|---|
| Deionized Water (pH 7.0) | Mean | 83 | 90 | 92 | 95 | 97 | 98 |
| | % RSD | 7.5% | 5.2% | 4.0% | 2.7% | 2.2% | 1.7% |
| 0.1N HCl (pH 1.2) | Mean | 81 | 87 | 88 | 91 | 93 | 95 |
| | % RSD | 10.0% | 8.7% | 7.3% | 5.5% | 4.3% | 3.2% |
| Acetate Buffer (pH 4.5) | Mean | 81 | 90 | 93 | 96 | 97 | 98 |
| | % RSD | 7.0% | 5.5% | 2.8% | 2.0% | 1.4% | 1.2% |
| Phosphate Buffer (pH 7.5) | Mean | 38 | 80 | 86 | 91 | 94 | 96 |
| | % RSD | 47.4% | 26.9% | 8.9% | 6.8% | 5.4% | 4.4% |

The results of Example 7 show that the dissolution profiles of the rapidly dissolving pharmaceutical composition tablets including 5 mg hydrocodone bitartrate and 400 mg guaifenesin and the reference products (TUSSIGON™ tablets including hydrocodone bitartrate and homatropine tablets, and OTC guaifenesin tablets) were demonstrated to be similar.

It will be understood that the present description illustrates those aspects of the invention relevant to a clear understanding of the invention. Certain aspects that would be apparent to those of ordinary skill in the art and that, therefore, would not facilitate a better understanding of the invention have not been presented in order to simplify the present description. Although only a limited number of embodiments of the present invention are necessarily described herein, one of ordinary skill in the art will, upon considering the foregoing description, recognize that many modifications and variations of the invention may be employed. All such variations and modifications of the invention are intended to be covered by the foregoing description and the following claims.

The following numbered clauses are directed to various non-limiting examples of inventions according to the present disclosure:

1. A rapidly dissolving pharmaceutical composition comprising an about 80:1 ratio of guaifenesin to hydrocodone bitartrate, further comprising one or more disintegrants, binders, lubricants, and/or glidants, provided that the rapidly dissolving pharmaceutical composition is uniform, wherein the rapidly dissolving pharmaceutical composition has a friability less than 1% and a relative standard deviation of the uniformity of dosage units of hydrocodone bitartrate is less than about 4%.
2. The rapidly dissolving pharmaceutical composition of clause 1, wherein the composition comprises from 1% to about 5%, by weight, of a disintegrant.
3. The rapidly dissolving pharmaceutical composition of clause 2, wherein the composition comprises from 10% to about 90% of a binder.
4. The rapidly dissolving pharmaceutical composition of clause 3, wherein the rapidly dissolving pharmaceutical composition comprises about 0.25% to about 5% of a lubricant.
5. The rapidly dissolving pharmaceutical composition of clause 4, wherein the rapidly dissolving pharmaceutical composition comprises about 0.1% to about 10% of a glidant.

6. A rapidly dissolving composition comprising an about 80:1 ratio of guaifenesin to hydrocodone bitartrate, further comprising one or more disintegrants, binders, lubricants, and/or glidants, provided that the rapidly dissolving pharmaceutical composition has a hardness between 6 and 12 Kp and a relative standard deviation of the uniformity of dosage units of guaifenesin is less than about 5%.

7. A rapidly dissolving composition comprising an about 80:1 ratio of guaifenesin to hydrocodone bitartrate, further comprising one or more disintegrants, binders, lubricants, and/or glidants, provided that the rapidly dissolving pharmaceutical composition has a friability less than 1% and a relative standard deviation of the uniformity of dosage units of hydrocodone bitartrate is less than about 4%.

8. A rapidly dissolving uniform composition comprising an about 80:1 ratio of guaifenesin to hydrocodone bitartrate, further comprising one or more disintegrants, binders, lubricants, and/or glidants, wherein after a period of at least 6 months at a temperature ranging from 23° C. to 27° C. and a relative humidity ranging from 55% to 65%, the rapidly dissolving pharmaceutical composition retains greater than about 90% of the hydrocodone bitartrate and greater than about 90% of the guaifenesin contained in the original composition.

9. A rapidly dissolving uniform composition comprising an about 80:1 ratio of guaifenesin to hydrocodone bitartrate, further comprising one or more disintegrants, binders, lubricants, and/or glidants, wherein after a period of at least 1 month at a temperature ranging from 38° C. to 42° C. and a relative humidity ranging from 70% to 80%, the rapidly dissolving pharmaceutical composition retains greater than about 90% of the hydrocodone bitartrate and greater than about 90% of the guaifenesin contained in the original composition.

10. A rapidly dissolving pharmaceutical composition comprising an about 80:1 ratio of guaifenesin to hydrocodone bitartrate, wherein at least 85 wt % hydrocodone bitartrate and at least 85 wt % guaifenesin contained therein are released after 15 minutes according to the USP Paddle Method at 50 rpm using a deionized water dissolution medium at about 37° C.

11. A rapidly dissolving pharmaceutical composition comprising an about 80:1 ratio of guaifenesin to hydrocodone bitartrate, wherein the pharmaceutical composition provides a guaifenesin $C_{max}$ ranging from about 6.89 µg/mL to about 7.57 µg/m L, following the oral administration of the pharmaceutical composition to a patient under fasting conditions.

12. Method of administering a rapidly dissolving pharmaceutical composition comprising guaifenesin to an adult human who has not ingested food within 60 minutes of administration, wherein the rapidly dissolving pharmaceutical composition provides a guaifenesin $C_{max}$ ranging from about 6.89 µg/mL to about 7.57 µg/m L.

13. Method of administering a rapidly dissolving composition comprising hydrocodone bitartrate to an adult human who has not ingested food within 60 minutes of administration, wherein the rapidly dissolving pharmaceutical composition provides a hydrocodone bitartrate $C_{max}$ ranging from about 2.09 µg/mL to about 2.49 µg/mL.

14. Method of administering a rapidly dissolving composition comprising guaifenesin to an adult human who ingested food within 30 minutes of administration, wherein the rapidly dissolving pharmaceutical composition provides a guaifenesin $C_{max}$ ranging from about 6.37 µg/mL to about 7.25 µg/m L.

15. Method of administering a rapidly dissolving composition comprising hydrocodone bitartrate to an adult human who ingested food within 30 minutes of administration, wherein the rapidly dissolving pharmaceutical composition provides a hydrocodone bitartrate $C_{max}$ ranging from about 2.15 µg/mL to about 2.55 µg/mL.

16. Method of administering an oral tablet comprising hydrocodone bitartrate and guaifenesin, wherein the $AUC_{0 \to \infty}$ does not substantially change from a food effect.

17. The composition of clause 1, wherein a remaining concentration of hydrocodone bitartrate is greater than about 90% by weight and a remaining concentration of guaifenesin is greater than about 90% by weight after the rapidly dissolving rapidly dissolving pharmaceutical composition has been stored for at least 6 months at a temperature ranging from 23° C. to 27° C. and a relative humidity ranging from 55% to 65%.

18. The composition of clause 1, wherein a remaining concentration of hydrocodone bitartrate is greater than about 90% by weight and a remaining concentration of guaifenesin is greater than about 90% by weight after the rapidly dissolving pharmaceutical composition has been stored for at least 1 month at a temperature ranging from 38° C. to 42° C. and a relative humidity ranging from 70% to 80%.

19. The composition of clause 1, wherein the lubricant includes at least two lubricants.

20. The composition of clause 1, wherein the composition includes about 5 mg of hydrocodone bitartrate.

21. The composition of clause 1, wherein the composition includes about 400 mg of guaifenesin.

22. A method comprising:
    administering a rapidly dissolving composition comprising guaifenesin and hydrocodone, or a pharmaceutically acceptable salt thereof, to an adult human who has ingested food within 30 minutes of administration, wherein the rapidly dissolving pharmaceutical composition provides a guaifenesin $AUC_{0 \to \infty}$ ranging from about 7.42 µg*h/mL to about 8.10 µg*h/m L.

23. The method of clause 22, wherein the hydrocodone comprises hydrocodone bitartrate.

24. The method of clause 22, wherein the rapidly dissolving composition includes 5 mg of hydrocodone bitrate.

25. The method of clause 22, wherein the composition includes about 400 mg of guaifenesin.

26. The method of clause 22, wherein the rapidly dissolving pharmaceutical composition provides a guaifenesin $C_{max}$ ranging from about 6.37 µg/mL to about 7.25 µg/mL.

27. The method of clause 22, wherein a remaining concentration of hydrocodone bitartrate is greater than about 90% by weight and a remaining concentration of guaifenesin is greater than about 90% by weight after the rapidly dissolving rapidly dissolving pharmaceutical composition has been stored for at least 6 months at a temperature ranging from 23° C. to 27° C. and a relative humidity ranging from 55% to 65%.

28. The method of clause 22, wherein a remaining concentration of hydrocodone bitartrate is greater than about 90% by weight and a remaining concentration of guaifenesin is greater than about 90% by weight after the rapidly dissolving rapidly dissolving pharmaceutical composition has been stored for at least 1 month at a temperature ranging from 38° C. to 42° C., and a relative humidity ranging from 70% to 80%.

29. A method of preparing tablets of a rapidly dissolving pharmaceutical composition comprising:

(i) preparing a hydrocodone blend including:
  adding layers to a blender, the layers comprising
    a first portion of microcrystalline cellulose,
    crospovidone,
    hydrocodone bitrate,
    talc,
    stearic acid and
    a second portion of microcrystalline cellulose; and
  blending the layers for 10 minutes at 15 rpm to form the hydrocodone blend;
(ii) preparing a first mixture, including:
  adding layers to a blender, the layers comprising
    a first portion of the hydrocodone blend,
    Compresso GGF 95 SA, and
    a second portion of the hydrocodone blend; and
  blending for 30 minutes at 15 rpm to form the first mixture;
(iii) adding magnesium stearate to the first mixture to form a final mixture; and
(iv) compressing portions of the final mixture into tablets.

What is claimed is:

1. A rapidly dissolving pharmaceutical composition comprising a uniform blend comprising:
  guaifenesin and hydrocodone bitartrate in a weight ratio of about 80:1 guaifenesin to hydrocodone bitartrate;
  a disintegrant comprising crospovidone;
  a binder comprising microcrystalline cellulose; and
  a lubricant comprising magnesium stearate, stearic acid, and talc;
  wherein the pharmaceutical composition comprises a tablet; and
  wherein a remaining concentration of hydrocodone bitartrate is greater than about 90% by weight of a starting concentration of hydrocodone bitartrate and a concentration of guaifenesin is greater than about 90% by weight of a starting concentration of guaifenesin after the pharmaceutical composition in the form of a tablet has been stored for at least 6 months at a temperature ranging from 23° C. to 27° C. and a relative humidity ranging from 55% to 65%.

2. The pharmaceutical composition of claim 1, wherein the lubricant further comprises at least one of calcium stearate, sodium stearate, maize starch, and corn starch.

3. The pharmaceutical composition of claim 1, wherein the tablet comprises a friability less than 1%.

4. The pharmaceutical composition of claim 1, wherein the tablet comprises a hardness of at least 5 Kp.

5. The pharmaceutical composition of claim 1, wherein a remaining concentration of hydrocodone bitartrate is greater than about 90% by weight of a starting concentration of hydrocodone bitartrate and a remaining concentration of guaifenesin is greater than about 90% by weight of a starting concentration of guaifenesin after the pharmaceutical composition in the form of a tablet has been stored for at least 1 month at a temperature ranging from 38° C. to 42° C. and a relative humidity ranging from 70% to 80%.

6. A rapidly dissolving pharmaceutical composition comprising a uniform blend comprising:
  guaifenesin and hydrocodone bitartrate in a weight ratio of about 80:1 guaifenesin to hydrocodone bitartrate;
  about 1% to about 5% by weight of a disintegrant comprising crospovidone;
  about 10% to about 90% by weight of a binder comprising microcrystalline cellulose; and
  about 0.25% to about 5% by weight of a lubricant comprising magnesium stearate, stearic acid, and talc;
  wherein the pharmaceutical composition comprises a tablet; and
  wherein a remaining concentration of hydrocodone bitartrate is greater than about 90% by weight of a starting concentration of hydrocodone bitartrate and a concentration of guaifenesin is greater than about 90% by weight of a starting concentration of guaifenesin after the pharmaceutical composition in the form of a tablet has been stored for at least 6 months at a temperature ranging from 23° C. to 27° C. and a relative humidity ranging from 55% to 65%.

7. The pharmaceutical composition of claim 6, wherein the lubricant further comprises at least one of calcium stearate, sodium stearate, maize starch, and corn starch.

8. A rapidly dissolving pharmaceutical composition comprising a uniform blend comprising:
  guaifenesin and hydrocodone bitartrate in a weight ratio of about 80:1 guaifenesin to hydrocodone bitartrate; and
  a lubricant comprising magnesium stearate, stearic acid, and talc;
  wherein the pharmaceutical composition comprises a tablet; and
  wherein a remaining concentration of hydrocodone bitartrate is greater than about 90% by weight of a starting concentration of hydrocodone bitartrate and a concentration of guaifenesin is greater than about 90% by weight of a starting concentration of guaifenesin after the pharmaceutical composition in the form of a tablet has been stored for at least 6 months at a temperature ranging from 23° C. to 27° C. and a relative humidity ranging from 55% to 65%.

9. The pharmaceutical composition of claim 8, wherein the binder further comprises at least one of maltodextrin, povidone, hydroxypropyl methylcellulose, hydroxyethyl cellulose, starch, pregelatinized starch, sorbitol, and sucrose.

10. The pharmaceutical composition of claim 8, wherein the tablet comprises a friability less than 1%.

11. The pharmaceutical composition of claim 8, wherein the tablet comprises a hardness of at least 5 Kp.

12. The pharmaceutical composition of claim 8, wherein the pharmaceutical composition includes about 400 mg of guaifenesin.

13. The pharmaceutical composition of claim 8, wherein the pharmaceutical composition comprises about 5 mg of hydrocodone bitartrate.

14. The pharmaceutical composition of claim 1, wherein the tablet comprises a hardness of 6 Kp to 12 Kp.

15. The pharmaceutical composition of claim 8, wherein the tablet comprises a hardness of 6 Kp to 12 Kp.

16. The rapidly dissolving pharmaceutical composition of claim 1, wherein at least 85 weight percent of the hydrocodone bitartrate and at least 85 weight percent of the guaifenesin in the tablet are released after 15 minutes according to a USP Paddle Method at 50 rpm using a deionized water dissolution medium at about pH 7 and about 37° C.

17. The rapidly dissolving pharmaceutical composition of claim 6, wherein at least 85 weight percent of the hydrocodone bitartrate and at least 85 weight percent of the guaifenesin in the tablet are released after 15 minutes according to a USP Paddle Method at 50 rpm using a deionized water dissolution medium at about pH 7 and about 37° C.

18. The rapidly dissolving pharmaceutical composition of claim 8, wherein at least 85 weight percent of the hydrocodone bitartrate and at least 85 weight percent of the guaifenesin in the tablet are released after 15 minutes according to a USP Paddle Method at 50 rpm using a deionized water dissolution medium at about pH 7 and about 37° C.

19. The pharmaceutical composition of claim 6, wherein a remaining concentration of hydrocodone bitartrate is greater than about 90% by weight of a starting concentration of hydrocodone bitartrate and a remaining concentration of guaifenesin is greater than about 90% by weight of a starting concentration of guaifenesin after the pharmaceutical composition in the form of a tablet has been stored for at least 1 month at a temperature ranging from 38° C. to 42° C. and a relative humidity ranging from 70% to 80%.

20. The pharmaceutical composition of claim 8, wherein a remaining concentration of hydrocodone bitartrate is greater than about 90% by weight of a starting concentration of hydrocodone bitartrate and a remaining concentration of guaifenesin is greater than about 90% by weight of a starting concentration of guaifenesin after the pharmaceutical composition in the form of a tablet has been stored for at least 1 month at a temperature ranging from 38° C. to 42° C. and a relative humidity ranging from 70% to 80%.

* * * * *